(12) United States Patent
Kubicek et al.

(10) Patent No.: US 9,573,917 B2
(45) Date of Patent: Feb. 21, 2017

(54) PROCESS FOR THE MANUFACTURE OF EPOXY-MONOMERS AND EPOXIDES

(71) Applicant: SPOLEK PRO CHEMICKOU A HUTNI VYROBU A.S., Usti nad Labem (CZ)

(72) Inventors: Pavel Kubicek, Decin (CZ); Bedrich Nemecek, Jilove u Decina (CZ); Petr Sladek, Utsi nad Labem (CZ)

(73) Assignee: SPOLEK PRO CHEMICKOU A HUTNI VYROBU A.S., Usti nad Labem (CZ)

( * ) Notice: Subject to any disclaimer, the term of this patent is extended or adjusted under 35 U.S.C. 154(b) by 0 days.

(21) Appl. No.: 14/897,241

(22) PCT Filed: Jun. 9, 2014

(86) PCT No.: PCT/CZ2014/000064
§ 371 (c)(1),
(2) Date: Dec. 10, 2015

(87) PCT Pub. No.: WO2014/198243
PCT Pub. Date: Dec. 18, 2014

(65) Prior Publication Data
US 2016/0122310 A1    May 5, 2016

(30) Foreign Application Priority Data

Jun. 10, 2013 (CZ) .............................. PV 2013-437

(51) Int. Cl.
*C07D 301/24* (2006.01)
*C07D 301/26* (2006.01)
*C07D 301/32* (2006.01)

(52) U.S. Cl.
CPC ........... *C07D 301/26* (2013.01); *C07D 301/32* (2013.01)

(58) Field of Classification Search
CPC .... C07D 301/26; C07D 301/32; C07D 301/24
(Continued)

(56) References Cited

U.S. PATENT DOCUMENTS 2,070,990 A    2/1937    Groll et al.
2,224,849 A    12/1940   Groll et al.
(Continued)

FOREIGN PATENT DOCUMENTS

DE    1041488    10/1958
DE    1226554    10/1966
(Continued)

OTHER PUBLICATIONS

International Search Report for International App. No. PCT/CZ2014/000064 dated Sep. 16, 2014.

*Primary Examiner* — T. Victor Oh
(74) *Attorney, Agent, or Firm* — Pearl Cohen Zedek Latzer Baratz LLP

(57) ABSTRACT

A process for manufacturing epoxy monomers and/or epoxides in high yields and useful quality and chemical stability by dehydrochlorination of the corresponding chlorohydrins with an alkaline agent, producing the corresponding side product dry salt in a high purity, characterized in that the process comprises the following steps: a. Reaction of the chlorohydrins with the alkaline agent to form corresponding epoxides and the corresponding precipitated chloride salt; b. Dehydration, and optionally completing the reaction, of the reaction mixture of step (a), by use of an azeotropic agent, added to step (b) or generated in situ in step (a), resulting in the producing of a dehydrated reaction mixture; c. Separating the resulting chloride salt by filtration from the dehydrated reaction mixture (b) and d. Isolating the epoxide from the filtered liquid fraction.

28 Claims, 11 Drawing Sheets

(58) Field of Classification Search
USPC .......................................................... 549/520
See application file for complete search history.

(56) References Cited

U.S. PATENT DOCUMENTS

| | | | |
|---|---|---|---|
| 2,248,635 | A | 7/1941 | Marple et al. |
| 3,247,227 | A | 4/1966 | White |
| 3,457,282 | A | 7/1969 | Polak et al. |
| 4,105,580 | A | 8/1978 | Sebag et al. |
| 5,198,117 | A | 3/1993 | Grierson et al. |
| 5,965,753 | A | 10/1999 | Masaki et al. |
| 6,156,941 | A | 12/2000 | Ikai et al. |
| 7,906,690 | B2 * | 3/2011 | Kruper, Jr. .............. C07C 29/62 568/841 |

FOREIGN PATENT DOCUMENTS

| | | |
|---|---|---|
| FR | 2912743 | 8/2008 |
| FR | 2917400 | 12/2008 |
| GB | 822686 | 10/1959 |
| RU | 2130452 | 5/1999 |
| WO | WO 2005/021476 | 3/2005 |
| WO | WO 2005/054167 | 6/2005 |
| WO | WO 2006/020234 | 2/2006 |
| WO | WO 2009/016149 | 2/2009 |
| WO | WO 2012/003519 | 1/2012 |

\* cited by examiner

PROCESS FOR THE MANUFACTURE OF EPOXY-MONOMERS AND EPOXIDES

CROSS-REFERENCE TO RELATED APPLICATIONS

This application is a National Phase Application of PCT International Application NO. PCT/CZ2014/000064, International Filing Date Jun. 9, 2014, claiming priortiy of Czech Republic Patent Application No. PV 2013-437, filed Jun. 10, 2013 all of which are incorporated herein by reference in their entirety.

TECHNICAL FIELD

The invention relates to a process for producing epoxy monomers and epoxides, especially of glycidol in high yield and purity, preferably in a continuous manner, prepared from monochloropropanediols, especially from bio renewable resources. It allows to obtain compositions of high quality glycidol and industrial useful dry salt or brine.

BACKGROUND ART

Glycidol is a versatile intermediate for further reaction, and has been known since the $19^{th}$ century.

However, the large scale use of glycidol has not been fully realized in the past due to its poor availability in required quantities and consequent higher cost for downstream applications. This invention concerns a new route to this potentially valuable intermediate, produced preferably in a continuous manner, in high quality and derived particularly from renewable resources, such as glycerine. In addition the proposed process also provides substantially pure salt or pure brine as side product, in high quality for commercial use. The glycidol produced is particularly of high quality and this enables conversion to better quality, more useful, derivatives, e.g. thermosets of polyols.

The most common method for production of glycidol involves the oxidation of allyl alcohol, which itself is prepared from mainly propylene oxide by an isomerisation process. The propylene oxide is prepared from propylene and an oxidation agent such as hydrogen peroxide, percarboxylic acid, hydroperoxides etc., catalyzed by various types of catalyst. The known disadvantages of this method are in the numerous reaction steps for preparation of allyl alcohol prior to its oxidation, the extraction of glycidol from obtained homogeneous aqueous reaction mixture containing unreacted allyl alcohol and by-products such as glycerol, acrolein, β-hydroxy propionic aldehyde, glycerol allyl ether and decomposition products of catalyst, and the purification of glycidol after its isolation from the aqueous solution. Moreover, the catalyst used, such as tungsten trioxide, decomposes during the oxidation and contributes to higher production costs.

The previous procedures moreover involved precursors derived from fossil oil.

Other approaches have been described using glycerine as the starting precursor. These approaches are now of growing interest, as glycerine is an important bio-derived by-product of the manufacture process for bio-diesel, itself an important development in the growing green-tech industry for, e.g. new transportation vehicles. Glycerine derived from this new route is available in feedstock quantities, however with a new profile of associated impurities as a consequence of its bio-diesel refinery preparation route. The impurities can be fatty acids, protein, and/or various ionic salts, the concentration of which in the glycerol varies according to the source of the biomass used.

Previous routes to glycerine came from fossil oil, via the propylene route, and thus, this invention preferably concerns the use of bio-derived glycerine with its consequent impurities, to prepare certain grades of glycidol in a cost effective, preferably continuous process. However, should other sources of glycerine become available in the future, the process would be still applicable.

One approach of the conversion of glycerine involves carbonation to glycerol carbonate, which product subsequently forms glycidol and $CO_2$, by decarboxylation of the carbonate. In the early 1950's, a new process for preparation of glycidol was developed involving the two-step synthesis by carbonylation of glycerol via glycerol carbonate. In the first step, a cyclic carbonate is transesterified with the glycerol in a solvent comprising an organic carbonate or mixture of carbonates, in the presence of a solid catalyst to form cyclic glycerol carbonate. The glycerol carbonate can also be prepared by carbamoylation of glycerol with urea, by oxidative carbonylation of glycerol with the mixture of carbon dioxide and oxygen, or by reaction of glycerol with phosgene under mild conditions (60 to 130° C., in the presence of a catalyst). The second step, i.e. thermic decarboxylation of glycerol carbonate is technologically more difficult. The reaction is usually kept at the temperature at 155 to 240° C. under vacuum to give glycidol and carbon dioxide, the yield of glycidol being about 60%, or with a basic catalyst. The reported yield of glycidol in the latter is over 80%, based on carbonate. Direct production of glycerol carbonate from glycerol and carbon dioxide under supercritical conditions or in the presence of tin or cerium catalysts has also been reported.

Glycerol carbonate is a relatively new material in the chemical industry, but one that could offer some interesting opportunities, as it can be prepared directly and in a high yield from glycerol. The advantage of the process for preparation of glycidol via glycerol carbonate is relatively simple two-step process. However, the lower yield of glycidol in the second step is considered to be the substantial disadvantage and attention has recently been paid to solve it. Therefore there is need to consider other routes.

Another route involves conversion of acrolein made from glycerol: WO2012/003519. In yet another approach, glycerine can be hydrochlorinated to monochloropropanediol, MCH, specifically the isomers 3-chloro-1,2-propandiol or 2-chloro-1,3-propandiol, using hydrogen chloride gas or aqueous hydrochloric acid. The MCH then can be converted to glycidol using alkaline agents yielding a reaction product mixture of the glycidol, corresponding salt and water (see, for example U.S. Pat. No. 2,070,990, U.S. Pat. No. 2,224, 849, DE 1041488, DE 1226554, U.S. Pat. No. 3,457,282, U.S. Pat. No. 5,965,753, GB 822686, U.S. Pat. No. 5,198, 117, U.S. Pat. No. 4,105,580, or U.S. Pat. No. 6,156,941). Historically, MCH was practically the first and only starting material for an industrial-scale preparation of glycidol. In fact, both MCH, as its isomers 3-chloro-1,2-propandiol or 2-chloro-1,3-propandiol, and glycidol itself were intermediates in the course of a multistage and expensive production of glycerol from allyl chloride via epichlorohydrin.

In order to purify the epoxy compound, azeotropic distillation has been employed to remove water (see, e.g. U.S. Pat. No. 2,248,635, U.S. Pat. No. 3,247,227, RU 2130452).

The modern process for production of glycidol starting from MCH is seen as a suitable technological alternative again. MCH can be now advantageously prepared by the recently developed technology of catalysed hydrochlorination of glycerine, as described in WO2005/021476, or WO2009/016149.

WO2009/016149 can be deemed as the closest prior art, hereafter cited as '149. The invention in '149 relates to a process for manufacturing glycidol comprising at least the following steps: a) glycerol and a chlorinating agent are reacted to form monochloropropanediol in a first reaction medium, following a preferred process described in WO2005/054167; and b) at least one basic compound is reacted with at least one part of the first reaction medium from step a) to form glycidol and a salt in a second reaction medium, the organic component of which has a monochloropropanediol content before reaction with the basic compound greater than 100 g/kg of organic component, following the processes described in FR 07/153375.

The object in '149 further is to obtain glycidol from MCH, at least one part of which was prepared by the reaction between glycerol and a chlorinating agent. The MCH as a starting material for glycidol synthesis may be isolated from reaction mixture, or the reaction mixture was used without purification. No particular reference is made that the starting with MCH which has very reduced impurities can yield useful production of glycidol. Low levels of ester or acid in the MCH are not described.

The reaction mixture in '149 after saponification was than treated to isolate glycidol, solvent and other organic components and to obtain purified glycidol-based product in the first step, while water and salt were isolated in the second step, or the water-based composition was recycled to an electrolysis process.

The art '149 further focuses on use of solvents to separate the glycidol from the reaction mixture. It is notable that amongst solvents quoted in '149, as suitable for use in the separation treatment of the formed glycidol and salt mixture, are such solvents as described below taken from the passage in '149:

The extraction solvent is generally such as described in Application FR 07/55697 by Solvay SA, of which the content, and more specifically the passage from page 10, line 23 to page 13, line 12, is incorporated here by reference. 'The extraction solvent is generally an organic solvent which may be chosen from epoxides other than glycidol, esters, ketones, ethers, alcohols, carboxylic acids, organic phosphates and phosphine oxides. The organic solvents may contain water, preferably up to saturation. Dichloropropanol, epichlorohydrin and mixtures thereof are particularly preferred extraction solvents.'

In order to minimise these multi issues and obtain useful yields of glycidol with limited impurities, and to obtain a substantially pure salt as a valuable by-product, we have achieved a process which can be optimised readily around a number of parameters.

Thus, the risk factors that can affect the yield of glycidol are many and some are described in the following:
  easy dimerization and rearrangement of glycidol,
  presence of water and too high temperature of epoxidation or presence of free basic- or acid-acting agents even at relatively low reaction temperature can increase the risk of polymerization, condensation or hydrolysis, possibly with the presence of the rest of salt in relatively low concentrations,
  above mentioned factors can be further complicated by serial reactions if there is prolonged residence time in process reactor,
  loss of glycidol during distillation by entraining to the solvent and water,
  low concentration of by-products is usually obtained during the saponification in diluted solutions; however, the higher the concentration of glycidol in the solution, higher is the content of by-products, which brings a significant problem in a continuous arrangement of reaction when carried out, e.g. in a CSTR reactor.
  at low reaction temperature, e.g. below 5° C., the rate of dehydrohalogenation is low and longer retention time of reaction is necessary, especially in case of 2-chloro-1,3-propandiol isomer,
  when using unrefined or poorly refined raw material (i.e. technical reaction mixtures) of the MCH, or indeed the starting glycerol from which MCH is derived, many impurities can become introduced into the reaction mixture and this causes problems with their removal, both from the glycidol and from the salt or brine,
  the reaction mixture containing glycidol and traces of salt is unstable and is useful only as an intermediate for immediate processing, because despite rapid neutralization, the content of glycidol can drop significantly, even at the low temperature, e.g. below 0° C.,
  in particular, actual kinetic trials show that during the addition of the sodium hydroxide solution, when the alkalinity of reaction mixture rises rapidly when system approaches the stoichiometric conditions, the mixture swells prior to reaching the equivalence point of—sodium hydroxide and MCH; this is connected with the formation of glycidyl ethers, glycerine a and polyglycerine, and (in case of processing in some alcohols) with formation of alkyl ethers of glycerol,
  subsequently the formation of undesired by-products is accelerated with the molar excess of sodium hydroxide to monochlorohydrin, especially in combination with elevated reaction temperature, which can also lead to spontaneous polymerization.
  extraction processes, as e.g. described in '149, can be used to isolate the glycidol from the reaction mixtures, instead of, for example distillation, in order to prevent the contact of the epoxide group with the sodium ions at elevated temperature; the disadvantage of such extraction processes is that there is the low efficiency of the separation in one step and the necessity of the multistage process for collecting a substantial portion of the glycidol. A part of organic compounds still remains in an aqueous phase containing ionic species, e.g. NaCl, and this makes the next processing impossible without an additional technological step. Thus the major problem in the extraction process is that the organic glycidol-rich phase still contains sodium ions which catalyse the degradation of the glycidol.

The next bottleneck is that the water-rich phase, which also contains ionic species, e.g. NaCl, still contains residual MCH and the rest of the glycidol, which must be recovered by further multistage extraction processes.

OBJECTIVES OF INVENTION

Definitions

Figure 1:
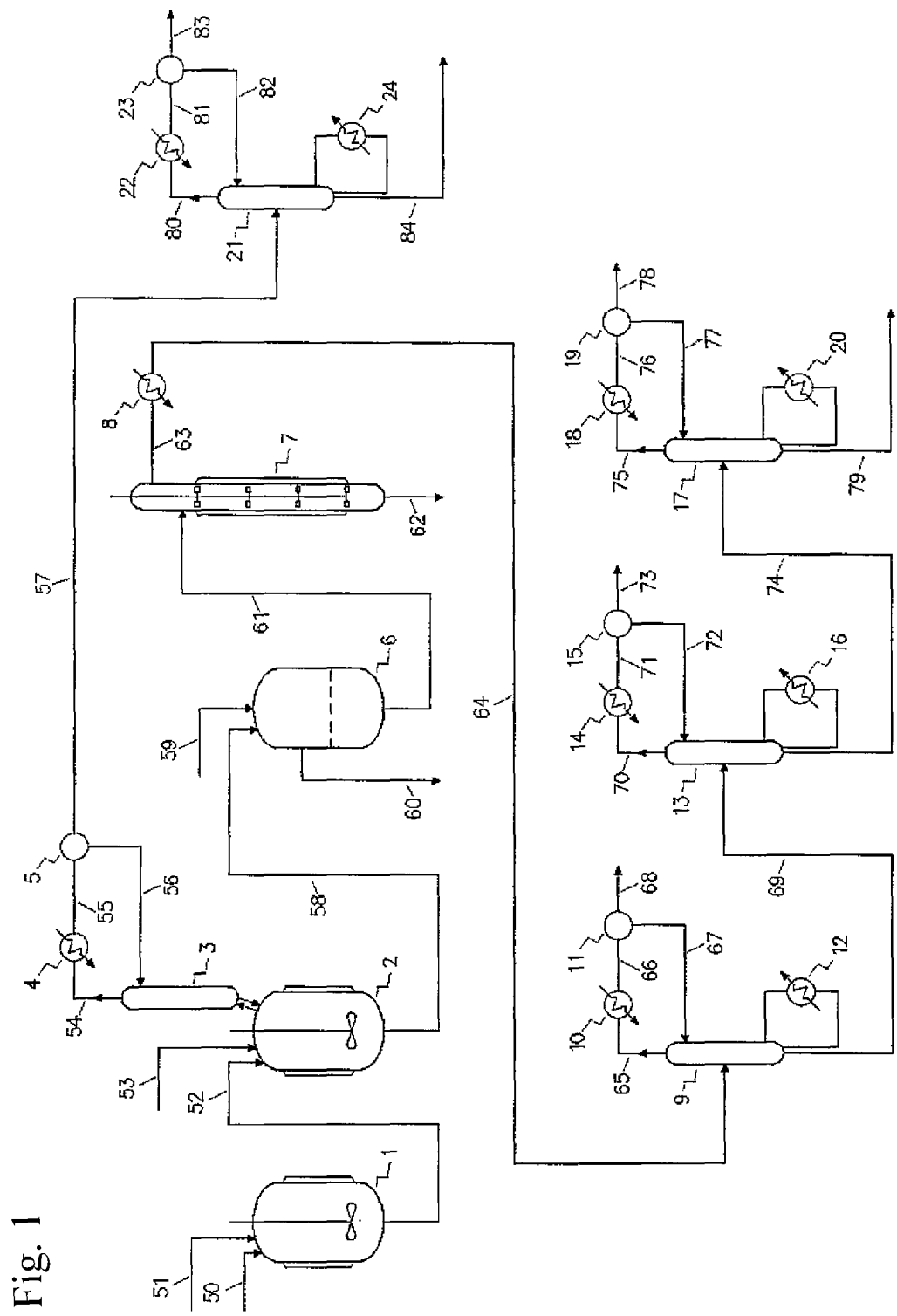
FIG. 1 depicts an overall process of the invention.
Figure 2:
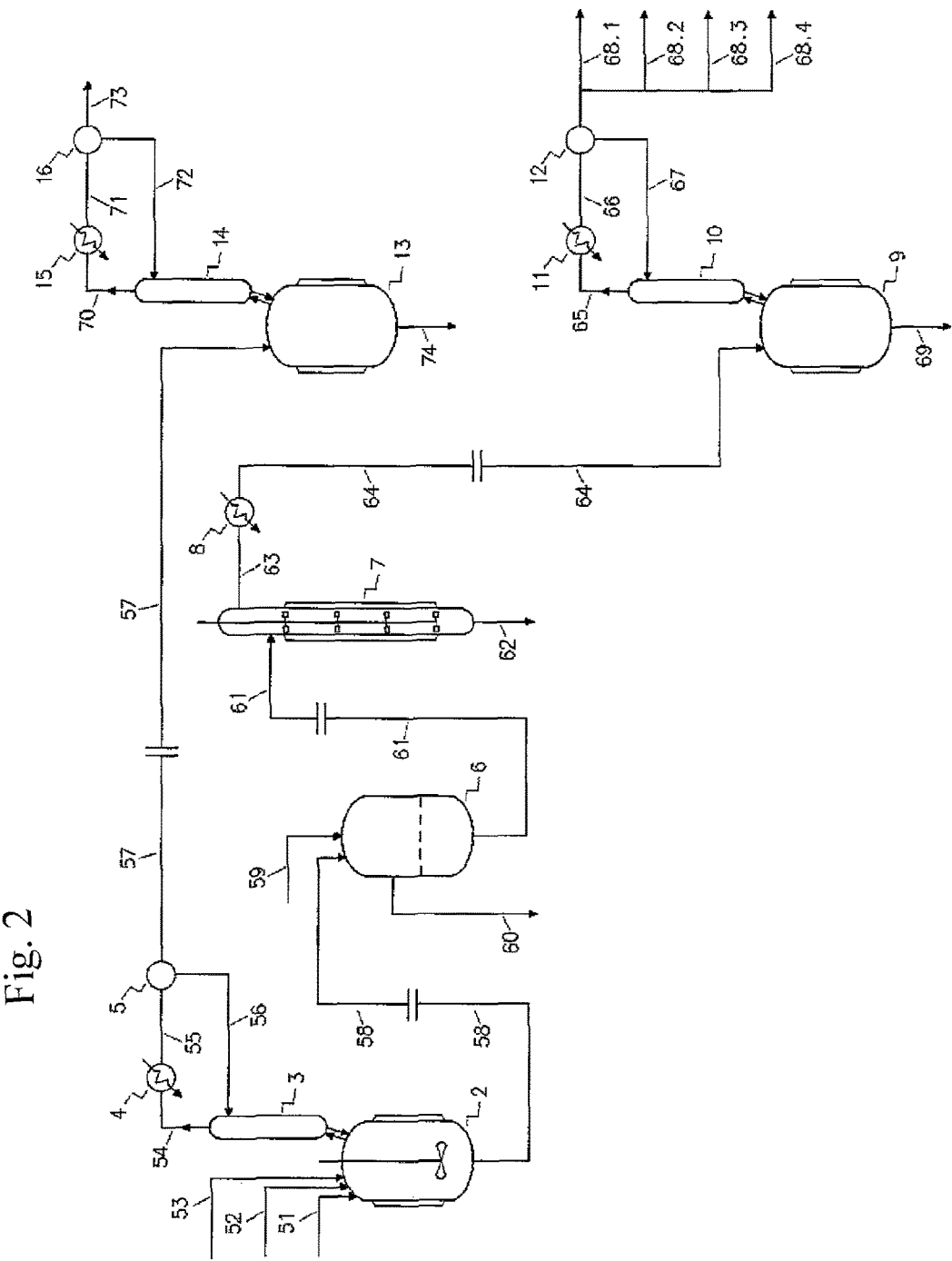
FIG. 2 depicts an overall batch process.
Figure 3:
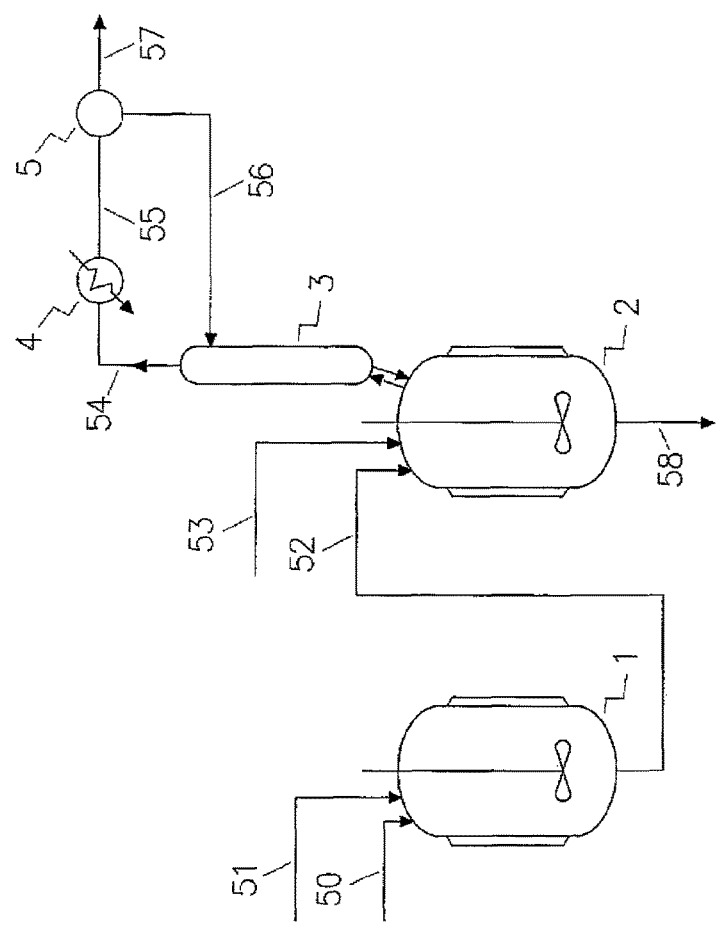
FIG. 3 depicts a continuous stirred tank reactor process.
Figure 4:
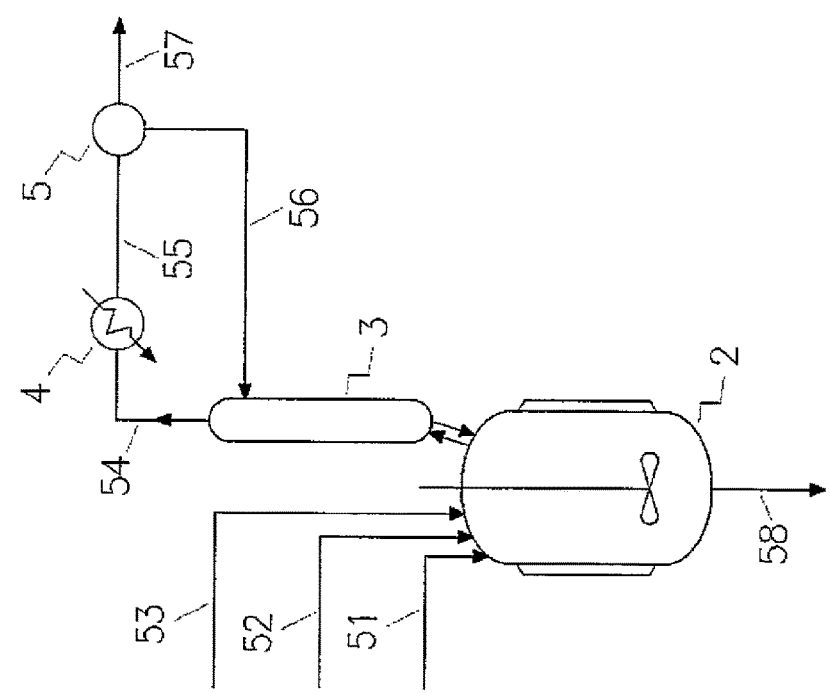
FIG. 4 is a scheme of a batch or semi-continuous process using a stirred tank reactor.
Figure 5:
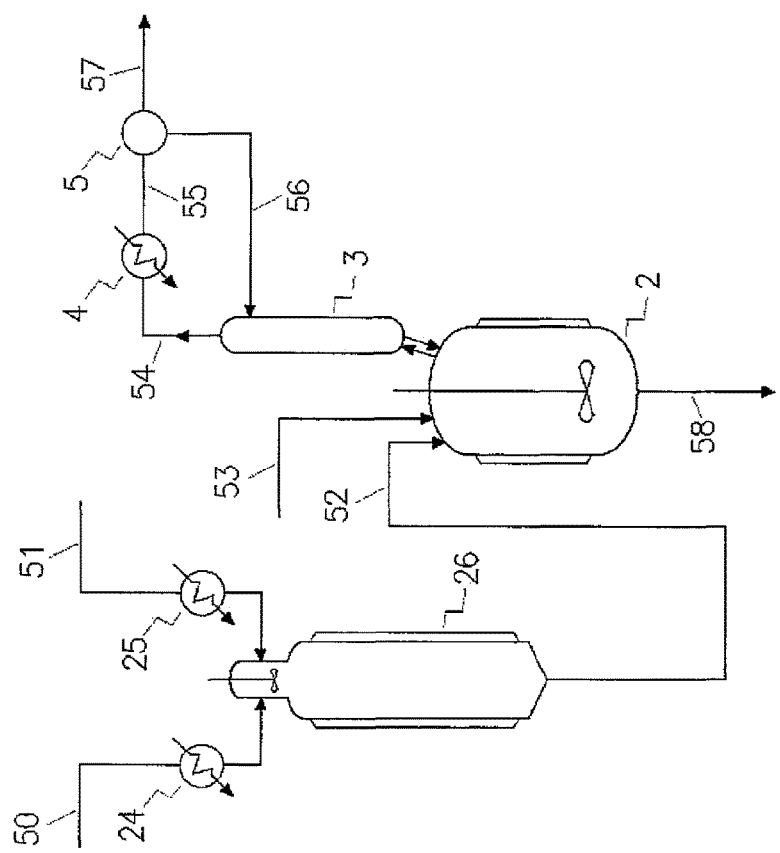
FIG. 5 depicts a continuous process with downwards flow.
Figure 6:
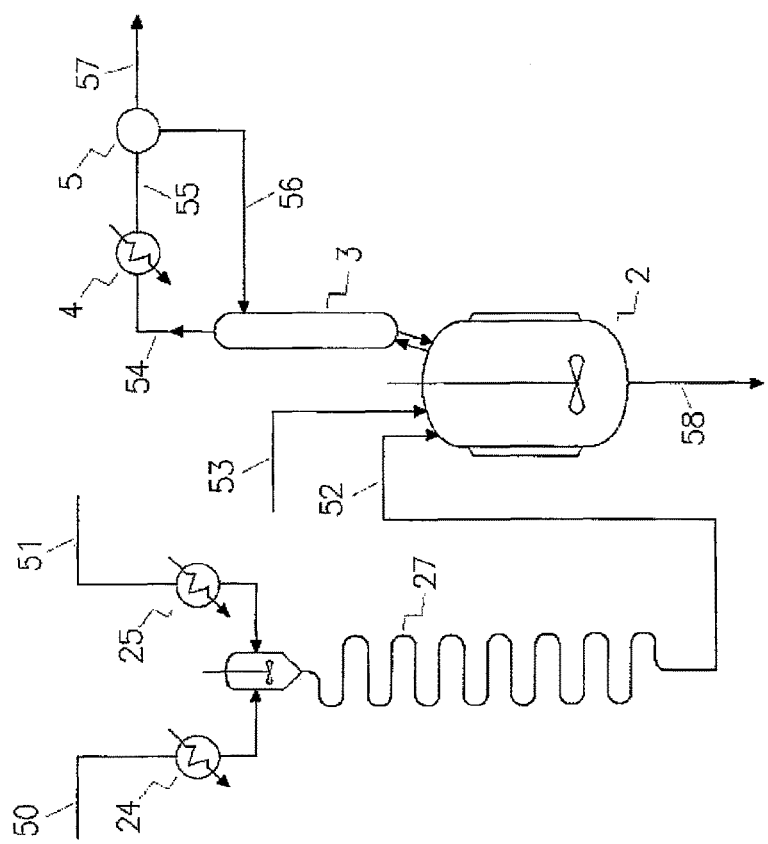
FIG. 6 depicts a continuous process using a plug-flow reactor without flow-direction limitation.
Figure 7:
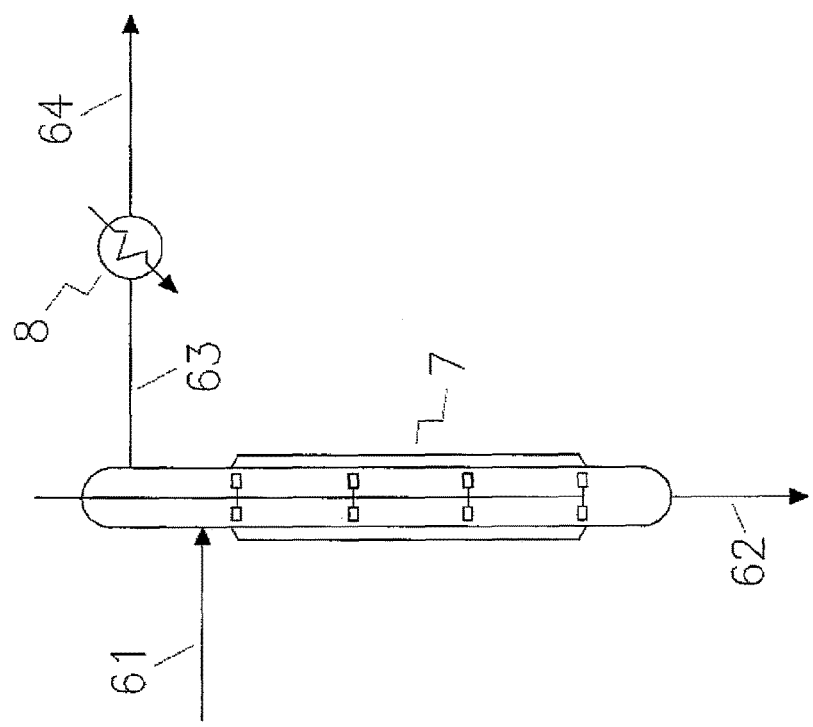
FIG. 7 is a scheme of continuous short residence time vacuum evaporation.
Figure 8:
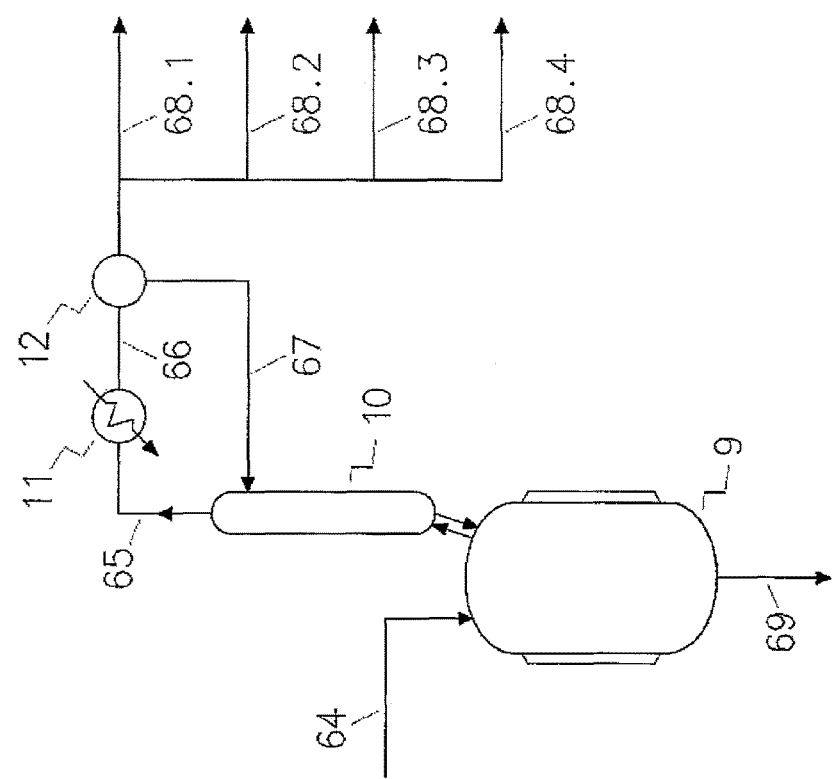
FIG. 8 illustrates a batchwise system of the distillation step.
Figure 9:
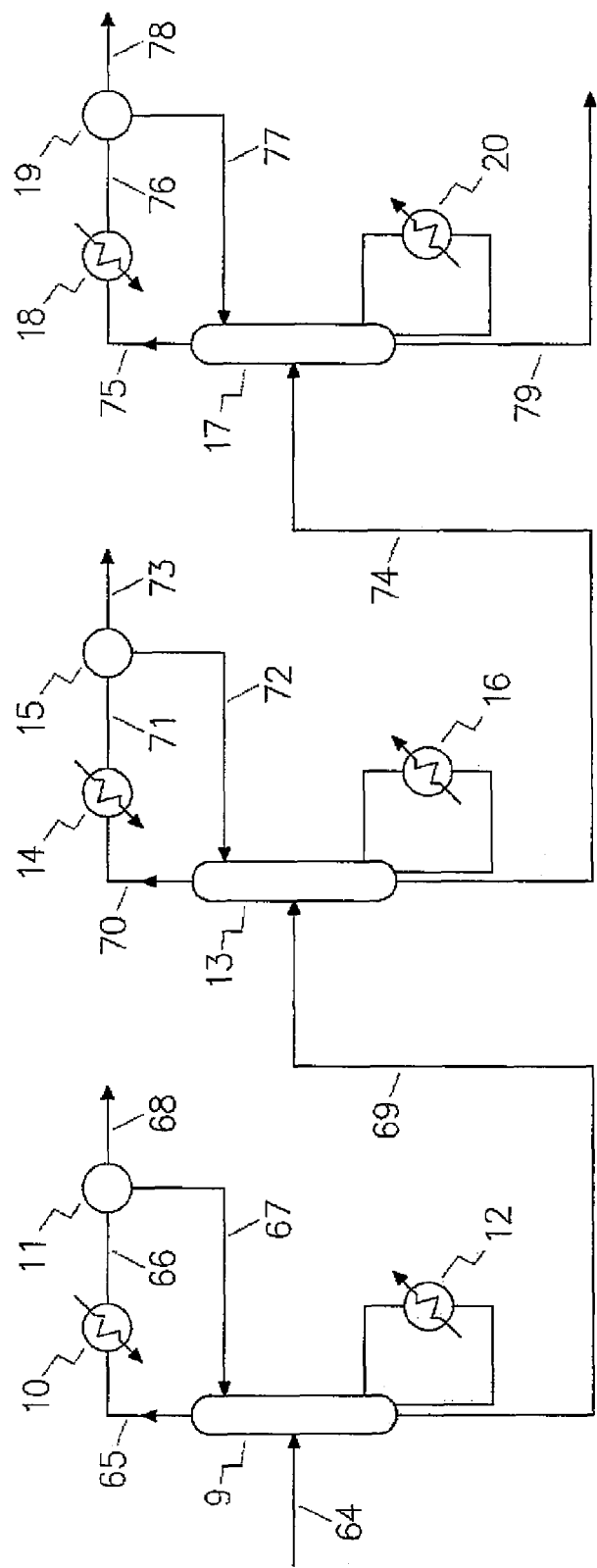
FIG. 9 illustrates a distillation step in a continuous system of three distillation columns.
Figure 10:
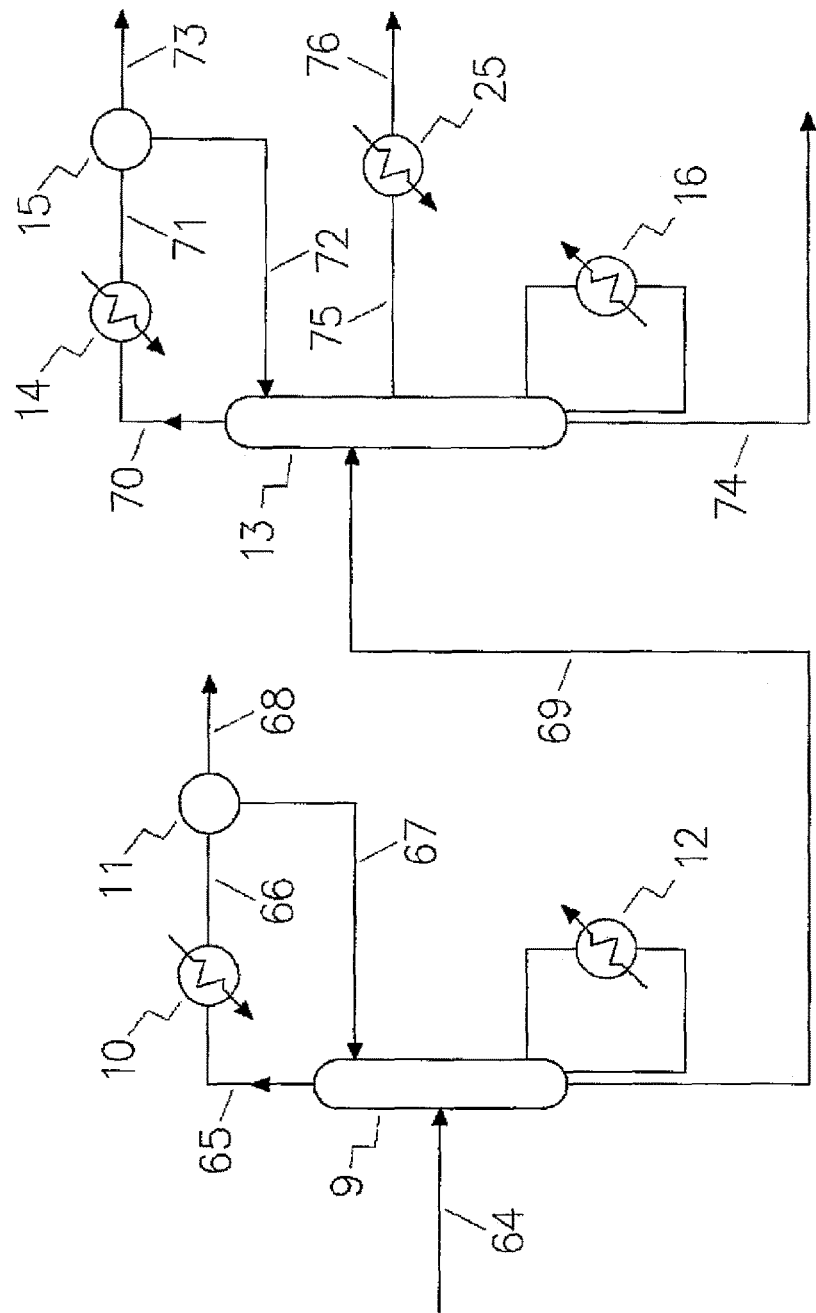
FIG. 10 illustrates a continuous vacuum distillation with two column arrangement.
Figure 11:
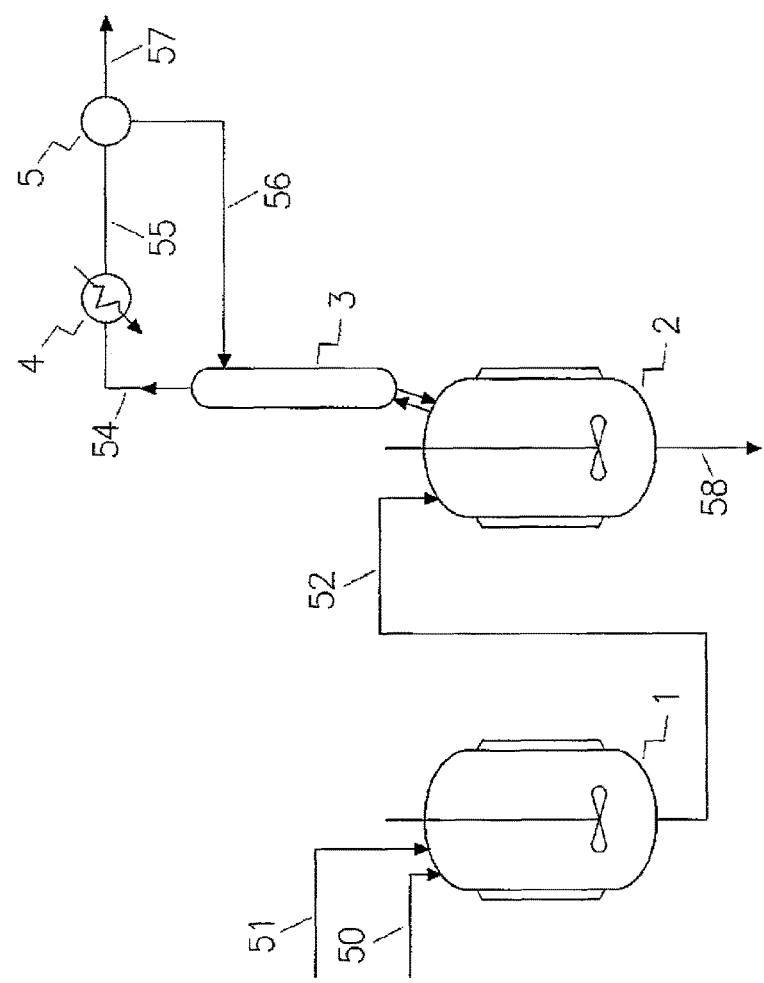
FIG. 11 is a scheme of the dehydration step.

The term "chlorohydrin" as used herein means the organic hydrocarbon with at least one pair of chloro- and hydroxyl-groups located on the vicinal carbons.

The term "monochloropropanediol" or "MCH" as used herein means 3-chloro-1,2-propanediol and/or 2-chloro-1,3-propanediol. The terms "3-chloro-1,2-propanediol" and "3-chloropropanediol" and "3MCH" are used herein as mutual equivalents. The terms "2-chloro-1,3-propanediol" and "2-chloropropanediol" and "2MCH" are used herein as mutual equivalents.

The term "dichloropropanol" or "DCH" as used herein means 1,3-dichloropropanol and/or 2,3-dichloropropanol. The terms "1,3-dichloropropanol" and "1,3-dichlorohydrin" and "13DCH" are used herein as mutual equivalents. The terms "2,3-dichloropropanol" and "2,3-dichlorohydrin" and "23DCH" are used herein as mutual equivalents.

The term "azeotropic agent" as used herein means an agent which forms a binary azeotropic mixture with water under the conditions as required for the current invention.

The term "ionic species" or "ionic impurity" as used herein means both organic and inorganic compounds containing alkali metal or alkali-earth metal in the molecule.

The term "TOC" means Total Organics Carbon content.

The term "GC" means Gas Chromatography analytical method.

It is an objective of the present invention to provide a process for manufacturing epoxy monomers and/or epoxides in high yields and useful quality and stability by dehydrochlorination of the corresponding chlorohydrins with an alkaline agent, producing the corresponding side product-dry salt in a high purity.

The present process consists of several, preferably continuous steps, finally resulting in pure epoxide compound, preferably glycidol, optionally together with epichlorohydrin, as product, with pure salt recovered as by-product and suitable for sale or for further treatment and processing, e.g. in chlor-alkali, e.g. diaphragm or membrane electrolysis process, and with small amount of undesired by-products. The process according to the present invention does not generate significant amount of waste water and moreover does not generate waste water containing salt, which means, it could be re-used as process water, diluting water, etc., in the other processes.

The process starts with chlorohydrins feedstock and uses an azeotropic agent during the next process step to effect recovery of the product glycidol and dry salt.

In a specific embodiment for obtaining highly pure glycidol and highly pure and easily processable dry salt the main process steps are as follows (see Scheme No. 1):
  alkaline de-hydrochlorination of chlorohydrins, e.g. MCH, this process occurring in the 'reaction zone'
  reaction mixture de-hydration by use of azeotropic agent and vacuum distillation azeotropic removal of water, this process occurring in the 'dehydration zone'
  salt filtration+salt purification (e.g. filter cake washing and drying),
  ionic compounds removal from the filtrate,
  filtrate separation to recover the azeoptropic agent to be recycled, to produce pure glycidol, to recover un-reacted chlorohydrin, e.g. MCH, to be recycled, and to separate undesired by-products.

It has been found by the present inventors that some type of alcohols, ketones and epoxides especially secondary and tertiary alcohols of low molecular weight, and some of their ethers, are very suitable 'dehydration' azeotropic distillation agents which work effectively in the envisaged process, also in a continuous mode, as described in this patent. Because of the high reactivity of the formed glycidol, the broad list of solvents quoted in '149 is not definitive enough. Moreover, '149 refers to extraction (involving separation based on liquid-liquid equilibrium), present process uses those compounds which are effective as azeotropic agent (involving separation based on non-ideal vapour-liquid equilibrium)

Moreover, '149 does not teach in detail how both the high purity of glycidol and high yield of glycidol is reached by that process. No example on this matter is present in '149.

Furthermore, there is no special mention in '149 that taking extreme care to remove any residual impurities, such as esters or halide impurities can lead to more stable and better yields of glycidol. The present invention found that alkali metal or alkali-earth metal species must be carefully removed before any thermal treatment, e.g. distillation, for the glycidol purification.

We have further determined that removing of the remaining very small amounts of ionic species, e.g. sodium ions, using a distillation process with short residence time, e.g. thin-film evaporation, considerably improves the chemical stability of the formed glycidol and thus its recovery in higher yield.

Moreover, surprisingly some primary alcohols, substituted primary alcohols, secondary and tertiary alcohols, used as the azeotropic agent in the next step, do not form significant amount of corresponding ethers using the process according to present invention—i.e. using the molar equivalent excess of chlorohydrins+acids to alkaline agent in the reactor feedstock.

Moreover it was found, that for continuous process, the reaction and dehydration zones should be separated to prevent the undesired by-product formation due to presence of alkaline agent, which is known as catalyst of many organics reaction, e.g. etherification or polymerization, in high concentration. Thus, for the continuous embodiment the reaction-dehydration process steps consist of (see Schemes 3, 5, 6):
  1. The first reaction zone, where the alkaline dehydrochlorination reaction takes place, without added azeotropic agent, and
  2. The second separate zone, where the dehydration step by distillation under reduced pressure by means of azeotropic agent takes place.

Thus a high yield of pure glycidol is obtained due to the double effect of both
  a) low reactivity of the selected azeotropic agent, e.g. some alcohols, ketones and epoxide, and
  b) setting up unfavourable conditions to form undesired by-product, e.g glycidylethers by etherification, in the dehydration zone, i.e. due to low content of the base catalyst and low temperature.

The critical step in the production of glycidol, from a route involving glycerine and chlorohydrins, is the dehydrohalogenation step. In this step, a chloride salt is usually formed: this invention shows that careful control of the liberated salt gives the required full reaction of chlorohydrin to glycidol, resulting in high yield at low operating conditions, which benefits greatly the stability of glycidol and thus its production in a preferable continuous process.

Moreover, starting with as pure as possible chlorohydrin, such as the monochlorohydrin, MCH, leads to useful production of the glycidol and also brine of high quality. The MCH derived from the glycerine route can contain some amounts of esters and poly-chlorohydroxy compounds and acids. Esters are formed from the reaction of the carboxylic acid catalysts with alcohols present in the system, poly-chlorohydroxy compounds are formed in higher extent by higher reaction temperatures. The present process can tolerate such impurities in the starting chlorohydrin, e.g. MCH, to produce substantially pure glycidol and the associated pure salt or brine.

Without wishing to be bound by theory, it is believed that the acid liberated from the esters mainly during the dehydrochlorination step can result in polymerisation of the glycidol and these heavy products can then contaminate the produced salt or can cause technical problem in process devices. Moreover, such acid can react with alkaline agent to form corresponding salts and subsequently can contaminate the resultant salt with negative influence on the salt or brine quality.

Many types of the alkaline agents, e.g. hydroxides, carbonates, alkoxides of alkali or alkali-earth metals can be used in the dehydrochlorination of chlorohydrins, e.g. MCH, and moreover, various kinds of solvents can be used. Among known disadvantages of the dehydrohalogenation when using basic agents, i.e. with an aqueous solution of sodium hydroxide, is the formation of undesired by-products, e.g. the condensation products of glycidol, and formation of 3-alkyl ethers of glycerol in alcohol-based solutions, even at low molar excess of a base-acting agent to the starting material and at mild temperature conditions between 0 and 40° C.

Another fundamental problem of such water-based dehydrochlorination is the separation of glycidol from a solution containing dissolved salts which catalyse glycidol degradation.

The length of time to distil the reaction water, as well the retention time of glycidol in contact with the sodium chloride solution at high temperatures, can be influenced by careful selection of a proper azeotropic agent.

The conditions for distillation of reaction water, especially the temperature and concentration of glycidol-salt slurry, can be significantly influenced with selection of a proper azeotropic agent.

Main Purposes for the Azeotropic Agent Usage are:
 efficient removal of water by the distillation, compared to distillation without azeotropic agent (more favourable vapour-liquid equilibrium)
 maintaining low temperatures in the distillation, especially at the bottom of the column respectively in the column boiler, where is the slurry of glycidol, water and sodium chloride. Higher temperature results in higher degree of polymerization
 adjusting of physical properties of such slurry like transport properties to allow efficient transport/handling+ filtration (viscosity etc.).
 for filtration, some solvent to wash the cake is required— so it is advantageous to use the same compound—no new solvents need to be handled or treated.
 lowering the boiling point of continuous thin-film evaporator (this agent also help to bring the temperature down)—again helps to fix the chemical stability issue The synergistic combination of purified chlorohydrins, e.g. MCH, highly selected azeotropic agent and essentially complete removal of ionic species enable a (preferable) continuous process for high yield, high quality epoxide, e.g. glycidol, and dry salt. Composition of the obtained high quality epoxide, e.g. glycidol, is described. This synergistic combination particularly enables commercially useful and environmentally efficient production of epoxides in high quality, selectivity and yield, e.g. for glycidol quality, which exceeds the quality of the commercially available product, preferably higher than 99.0%, more preferably higher than 99.5%, and the most preferably higher than 99.9% and for glycidol overall yield more than 90%, more preferably more than 95%.

Accordingly, this invention provides a process for manufacturing epoxy monomers and/or epoxides in high yields and useful quality and stability by dehydrochlorination of the corresponding chlorohydrins with an alkaline agent.

DISCLOSURE OF INVENTION

The present invention consists in a process for manufacturing epoxy monomers and/or epoxides in high yields and useful quality and stability by dehydrochlorination of the corresponding chlorohydrins with an alkaline agent, producing the corresponding side product dry salt in a high purity, which process comprises the following steps:
 a. Reaction of the chlorohydrin with the alkaline agent to form corresponding epoxides and the corresponding precipitated chloride salt;
 b. Dehydration, and optionally completing the reaction, of the reaction mixture of step (a), by use of an azeotropic agent, added to step (b) or generated in situ in step (a), resulting in the producing of a dehydrated reaction mixture;
 c. Separating the resulting chloride salt by filtration from the dehydrated reaction mixture (b), and
 d. Isolating the epoxide from the filtered liquid fraction.

This invention can be preferably used for preparing the glycidol or glycidol and epichlorohydrin resulting in high yields and useful quality and stability, and at the same time, resulting in high yield and useful quality of the side product, dry salt, by the dehydrochlorination of chlorohydrins, for example monochloropropanediols, MCH, comprising 3-chloro-1,2-propanediol and/or 2-chloro-1,3-propanediol, and dichloropropanols, DCH, comprising 1,3-dichloropropanol and 2,3-dichloropropanol, with an alkaline agent, in at least one continuous or batch process, involving at least a reaction step and a product separation step, where the latter step comprises at least one combination of sub-steps comprising a dehydration step, a filtration step, and at least one distillation step, with optional recycling of at least one of the resulting intermediate distillates to the reaction step (see Scheme No. 1, 2).

Preferably the dehydration sub-step comprises the addition of an azeotropic agent or its generation in situ in the reaction dehydrochlorination zone.

This azeotropic agent is preferably an organic compound forming a heterogeneous azeotropic mixture with water with the lower boiling point then water and/or agent and forming two separated liquid layers, i.e. agent is partially or totally immiscible with water. They can be selected from but not limited to alcohols or their ethers, epoxides, ketones, aliphatic or aromatic hydrocarbons, chlorinated hydrocarbons, etc.

The azeotropic agent itself or its generation in situ in the reaction dehydrochlorination zone, should have very low or zero ionic or reactive impurities under the conditions of present process.

The selected azeotropic compound preferably does not substantially react with the produced epoxides and starting chlorohydrins, e.g. glycidol and/or the MCH, and/or alkaline agent under process conditions according to present invention. Preferably the azeotropic compound is a compound with low molecular weight, with normal boiling point (i.e. the boiling point at the atmospheric pressure) less than 150° C., and does not form an azeotropic mixture with glycidol.

The mixture of the azeotropic agents can be also used, e.g. mixture of n-butanol and iso-butanol.

Bio-derived azeotropic agents, such as bio-derived isobutanol or n-butanol, are particularly useful in order to make the whole process more environmentally compatible and give glycidol with high content of renewable carbon.

Preferably the at least one distillation step uses a continuous or semi-continuous short residence time evaporation system such as a thin-film evaporation system, preferably agitated or wiped-film evaporation system or short-path evaporation system, operated under reduced pressure in range 0.1-100 torr, more preferably 1-10 torr.

The process can be carried out using the following reaction steps and zones:

Reaction Zone:

The dehydrochlorination reaction of the chlorohydrins with a base is carried out in this zone. The detailed conditions are described below.

Product Separation Zone:

The reaction mixture of the dehydrochlorination, from the reaction zone which may be batch or continuous, is fed into a product separation zone, comprising the following sub-zones:

1. A dehydration sub-zone involving a vacuum distillation device, preferably distillation column with accessories, where the azeotropic agent is added, preferably to the column bottom, more preferably to the boiler, to efficiently remove water, to aid in almost complete precipitation of the salt from the reaction mixture, and to assist in the removal of water in the distillation step. The reaction mixture is preferably fed to the column boiler. Column reboiler can be various design suitable for slurry handling, e.g. stirred tank with heating elements, thin-film evaporator, thermosyphon shell and tube or forced-flow shell and tube. Preferred type is stirred tank with heating elements, e.g. heating jacket, or forced-flow shell and tube reboiler.

2. A filtration sub-zone, where the dehydrated reaction mixture consisting of the resultant glycidol, the dehydration azeotropic agent, the precipitated salt and small amount of water is filtered to remove the precipitated salt. Filtration device can be various design suitable for salt slurry filtration, like pressure filter, candle filter, membrane filter, various centrifuges, decanters, press filters, etc. Part of the filtration device is a device for filter cake drying and solvent (=azeotropic agent) recovery. If the dry pure salt with content of TOC significantly below 100 mg/kg is required as a by-product, additional multistep washing/filtering and drying using appropriate solvent or high temperature oxidizing treatment is used, with the temperature in range 400-800° C., more preferably 500-600° C. As the source of oxygen air, oxygen rich air, oxygen in mixture with other inert gases or pure oxygen can be used. If the ultra-pure saturated or concentrated brine with content of TOC below 10 mg/kg is required, additional wet catalytic oxidation process is used with temperature range 0-200° C. Source of oxidizing agent can be oxygen, ozone or the mixture with oxygen, various hypochlorites, hydrogen peroxide, etc.

3. At least one distillation sub-zone where the filtered mixture of glycidol, dehydration azeotropic agent, small amount of water and remaining ionic species in form of salt and/or alkaline species, and some residual reaction liquids, are evaporated under reduced pressure in any device which promotes a short residence time in the liquid phase. A short residence time is found important to reduce any degradation of the glycidol product. Such a device is preferably a thin-film evaporator, preferably agitated thin-film evaporator, and the vapours leaving such an evaporation system can be condensed to collect liquid distillate as a liquid feed for the next separation sub-zone or can be directly used as a vapour feed to the next separation sub-zone. The distillation residue is a slurry consists mainly of ionic species, polymeric glycidol and traces of MCH.

4. At least one vacuum distillation sub-zone where the liquid or vapour distillate from the sub-zone 3 is continuously or batch-wise separated into the following streams/fractions:

4.1. at least one fraction containing residual water and/or azeotropic agent, 4.2. at least one fraction consists of substantially dry water-free azeotropic agent with traces of glycidol, 4.3. at least one fraction consists of substantially pure glycidol as a product, 4.4. at least one fraction consists of mixture of unreacted MCH with some glycidol and glycerine-based ethers (MCH recovery)

4.5. at least one fraction consists of undesired by-products.

The following recycling steps are applied:

Fraction 4.1. to be recycled back to sub-zone 1 or 2, preferably to sub-zone 1

Fraction 4.2. to be recycled back to sub-zone 1

Fraction 4.3. to be collected as a pure glycidol product

Fraction 4.4. to be recycled back to reaction zone

Fraction 4.5. to be partially recycled back to reaction zone and/or to be further treated.

Organic polyolic by-products are the final distillation residue. It can be with or without further treatment used as a polyol bio-based feedstock in a resin and polymer chemistry. The type of such treatment depends on final application request and content of chlorinated compounds in such distillation residue. The treatment can consist of chemical one (e.g. alkaline treatment) and/or physical one (e.g. distillation).

The distillation residue can be also disposed off in common ways like incineration, etc.

The described embodiment of the process refers preferably to continuous mode. However, in case of lower quantity of glycidol being acceptable, a batch embodiment can be advantageously used (see Scheme No. 2). In such batch process, the reaction and dehydration zone can be integrated and executed in a device which consists of a stirred reactor which also functions as boiler, and has a distillation column with accessories, which is linked to the reactor device. In this embodiment the feedstock chlorohydrin, e.g. MCH, is directly fed to the reactor together with azeotropic agent in appropriate ratio. After that, the vacuum distillation is started, so that azeotropic agent starts to circulate between column and reactor (boiler), at this stage no water is still formed. After this stage, the feedstock alkaline agent, preferably concentrated caustic soda solution, is semi-continuously fed to the reactor for appropriate time period. In this stage, water of reaction is formed and, together with water introduced together with alkaline agent, is distilled off using the azeotropic agent distillation. The distillate forms two liquid layers, the water-rich layer is withdrawn, azeotropic agent-rich layer is recycled back to the column. The formed epoxide, e.g. glycidol, and corresponding salt remain completely in the reactor together with azeotropic agent, which helps to keep slurry in the pumpable phase. By the term "pumpable" is meant that the mixture containing precipitated salt is not set solid or high viscous or sticky slurry to be stirred in the reactor and to be pumped out of the reactor. It is absolutely essential, like in continuous embodiment, that the sum of chlorohydrins and acids towards alkaline agent molar equivalent ratio remains above 1 to avoid significant side-product formation or, in worst case, spontaneous polymerization. Moreover, in this case no further neutralization is required, as the residual alkalinity is suppressed by the excess of chlorohydrins. The azeotropic agent, leaving the process via distillate in water-rich phase, can be compensated semi-continuously during the alkaline agent feed or just from the beginning by adding of such compensated amount directly to the reactor as a feed. Azeotropic agent from such water-rich phase can be recovered by other additional distillation. After completion of reaction the mixture of epoxide, e.g. glycidol, salt, azeotropic agent and small amount of water is withdrawn and processed using the same process units, i.e. filtration, thin-film short residence time distillation, and final vacuum distillation, which gives the required fractionating to form same fractions described in process description.

Reaction Parameters in Reaction Zone:

The dehydrochlorination can be carried out in a continuously operating reactor or in a cascade of continuous flow reactors suitable for suspension/slurry handling.

For continuous process, there can be used namely, but not limited to, continuous stirred tank reactor (CSTR—see Scheme No. 3) or plug-flow reactor (PFR) with downwards flow, which enables the precipitated salt can flow down together with liquid and does not accumulate in the system (see Scheme No. 5). Also PFR with very low diameter-to-length ratio, which can avoid precipitated salt accumulation due to higher velocities, can be used without flow-direction limitation (see Scheme No. 6). It is essential that, preferably for PFR, the inlet feedstocks chlorohydrin and alkaline agent are cooled down to slow the reaction rate especially during the mixing of such feedstock, where the local concentration gradients are formed resulting in undesired hot spots, and to allow the proper control of reaction rate and heat removal due to exothermic dehydrochlorination reaction. Dilution of some of inlet feedstock by water is another way to better control the reaction rate. Combination of dilution and cooling is also preferred embodiment especially for PFR reactor system.

Batch or semi-continuous process can be carried out in the reactor suitable for suspension/slurry handling, optionally acting as a boiler of dehydration too. As an example, stirred tank reactor (STR) can be used (see Scheme No. 4). All of the reactors should be equipped with heat transfer area.

For achieving favourable yields of the epoxide, e.g glycidol product, it is necessary, apart from the appropriate temperature and residence time, to keep a similar molar equivalent ratio of the sum of chlorohydrins and acids with regard to the alkaline agent in the reactor feedstock.

We found, for the continuous process, such ratio should be above 1.001, preferably between 1.001 and 1.30, more preferably between 1.01 and 1.25, the most preferably between 1.05 and 1.15. Ratio higher than 1.30 does not bring significant increase in yield, and furthermore the cost for unreacted MCH recovery becomes an increasing burden in the total process.

We also found, for the batch process, such ratio should be above 1.001, preferably between 1.001 and 1.15, more preferably between 1.002 and 1.05, the most preferably between 1.003 and 1.02. Higher ratio than 1.15 does not bring significant increase in yield, and furthermore the cost for unreacted MCH recovery becomes an increasing burden in the total process.

We also found the excess of alkali with combination of thermal treatment can lead to serious uncontrolled exothermic spontaneous polymerization, which are very hazardous. Next we also found the excess of alkali can lead to significant contamination of produced salt with various salts of carboxylic acid or their esters used in production of MCH feedstock by hydrochlorination of glycerine, which brings significantly higher cost for the salt treatment/purification.

Thus the molar equivalent excess of chlorohydrin, e.g. MCH, (surplus) is very important feature of present invention because of yield, reaction control and safety and salt quality especially in continuous operation.

Chlorohydrins Feedstock:

The liquid feed to the starting reaction zone contains at least 80% by weight of chlorohydrins monochloropropanediols, e.g. MCH or MCH+DCH, prepared by hydrochlorination of glycerol with hydrochloric acid and/or hydrogen chloride, which maybe catalysed, e.g. by carboxylic acid, or heterogenous catalysts. It can contain both inorganic and organic acids, e.g. hydrochloric acid and carboxylic acid. It can be diluted by water, however such 80% refers to the organic composition basis only—water excluded.

Preferably, the liquid feed contains 90-100% by weight of chlorohydrins, e.g. MCH or MCH+DCH, which can be prepared by catalytic hydrochlorination of glycerine using hydrochlorinating agent containing HCl and carboxylic acid as catalyst. The feedstock can consists of both isomers of MCH and DCH, which are produced by such hydrochlorination process starting from glycerine. It can be diluted by water, however such 90-100% refers to the organic composition basis only—water excluded.

The ratio of 2-chloro-1,3-propanediol towards 3-chloro-1,2-propanediol in the feedstock can vary according the upstream hydrochlorination process details and conditions. However it was found that the process efficiency according to present invention in term of glycidol yield surprisingly depends on such ratio. It is highly preferred to reduce the amount of 2-chloro-1,3-propanediol 2MCH in feedstock below a certain limit to keep the present process efficient.

Thus, the ratio 2MCH:3MCH in the feedstock should be lower than 1.0, more preferably lower than 0.25, even more preferably lower than 0.1 and the most preferably lower than 0.04.

The ratio of MCH towards DCH in the chlorohydrin feedstock can vary according the upstream hydrochlorination process details and conditions. However it was found that the process feasibility, according to present invention in term of efficiency, technical and mechanical problems, surprisingly depends on the MCH:DCH ratio in the chlorohydrin feedstock: it is highly preferred that such ratio should not substantially lie below 0.8:1.2.

Chlorohydrin feedstock can also contain some esters of carboxylic acids coming from the hydrochlorination process. The content of such esters can vary from 0-10%, more preferably 0-5%, the most preferably 0-1%. Water content can vary according to hydrochlorination process feedstock and conditions between 0-60%, preferably 0-40%, more preferably 0-30% and the most preferably between 0-10%.

Various chlorohydrins production processes are involved. There are three basic product combinations, or chlorohydrin process arrangements, reflecting the MCH to DCH (i.e. producing respectively glycidol GLD to epichlorohydrin ECH) ratio requirements. Some of them can produce solely MCH (going to GLD), some of them can produce either MCH and/or DCH (going to ECH). The processes also differ in the source of hydrochlorination agents.

It is advantageous to prepare MCH for use not only for the present purpose (i.e. glycidol GLD), but also for use in a two-step hybrid process for production dichloropropanol, DCH, and thus further on epichlorohydrin, ECH, from glycerine.

In the first hydrochlorination process embodiment, MCH is prepared by hydrochlorination of glycerine using concentrated hydrochloric acid solution with concentration range 19-37%, preferably 32-37%, the most preferably 34-37%, catalyzed by carboxylic acid with the concentration of the acid related to fed glycerine in range 0.1-10%, more preferably 0.2-5.0%, the most preferably 0.5-2.0% at the temperature in the range 100-140° C., ideally 130-140° C., to produce crude MCH.

This crude MCH leaves this initial system as a liquid product from the reactor zone comprising the glycerine, catalyst and the hydrochloric acid, contains water and is contaminated in the main by some DCH, unreacted HCl and some esters arising from the carboxylic acid catalysts.

The catalyst can be chosen according to the requirements of the process and described herein. Suitable ones are described in WO2005/054167.

The crude MCH product stream can be optionally dehydrated by means of distillation under reduced pressure and then can be further split into two production streams:
  the first stream dedicated for purification and subsequently production of glycidol by alkaline dehydrochlorination according to present invention;
  the second stream for use in the production of dichloropropanols, DCH, according to WO2005/021476, and other following art, where the feedstock to the process comprises the mixture of MCH, DCH and/or some water/HCl.

An efficiently integrated production process is thus provided, using readily transportable hydrochloric acid and glycerine as feedstocks.

In the new process for production of MCH, gaseous HCl is not required, and further, the subsequently produced DCH from MCH needs only about 50% less gaseous HCl.

The second preferred process for MCH and/or DCH production is an integrated three-step process which consists of the following process steps:
  Step 1: Distillation of concentrated hydrochloric acid with concentration range 32-37%, preferably 33-37%, the most preferably 36-37%, to produce HCl gas as a top vapour distillate and azeotropic hydrochloric acid as a bottom distillation residue under elevated pressure in range 0.15-1.0 MPa, more preferably 0.2-0.8 MPa, even more preferably 0.3-0.7 MPa and the most preferably 0.4-0.6 MPa.

Step 2: Hydrochlorination of glycerine with such azeotropic hydrochloric acid concentration range 18-22%, preferably 18.5-21%, the most preferably 18.9-19.5%, catalyzed by carboxylic acid with the concentration of the acid related to fed glycerine in range 0.1-10%, more preferably 0.2-5%, most preferably 0.5-2.0% at a temperature in the range 100-140° C., ideally 130-140° C., to produce crude MCH. The crude MCH product stream can be split into several production streams: the first stream dedicated for purification and subsequently production of glycidol by alkaline dehydrochlorination according to present invention, to the second stream consist of crude MCH to be dehydrated by distillation under reduced pressure, wherein dehydrated mixture is used as a feedstock in the production of dichloropropanols in the next step and water with content of DCH and HCl can be put together with primary distillate according to WO2005/021476 or processed directly in alkaline dehydrochlorination in ECH synthesis.

Step 3: Hydrochlorination of such dehydrated MCH production stream with gaseous HCl with content of HCl in range 99-100%, catalyzed by carboxylic acid with the concentration of the acid related to fed MCH in range 0.1-10%, more preferably 0.2-5%, the most preferably 0.5-1.0% at a temperature in the range 100-140° C., ideally 115-125° C., to produce crude DCH according to WO2005/021476, and other following art.

This modified process does not need external HCl gas source and can be supplied by concentrated hydrochloric acid only, wherein the HCl gas is generated in the process to supply the DCH production unit. Such process can be also utilized for DCH (further ECH) production only, so that no glycidol is produced in case all MCH formed in Step 2 is processed in the Step 3 in the production of DCH.

The third preferred arrangement of MCH production process is then its integration directly to the process for the production of DCH, preferably according to WO2005/021476, or into any other related schemes, e.g. WO2005/054167, WO2006/020234, etc. Further, the DCH line can be integrated into a dehydrochlorination step to produce epichlorohydrin, ECH.

In one embodiment, the processes according to previous inventions, e.g. WO2005/021476, can be advantageously modified by inserting another vacuum distillation step, which will further process a part of the distillation residue from the original distillation zone dedicated for water removal.

Such balanced part of distillation residue from primary vacuum water-distillation step will be distilled to produce following fractions:
  a dichloropropanol-rich fraction as a distillate which is returned back to the reactor system,
  a DCH and/or MCH pure product fraction as a side stream which is further processed to desired product and,
  a MCH-rich fraction as a distillation residue returned back to the reactor system.

This new integrated process allows to produce a wide ratio range for both MCH and DCH quality for further processing, e.g. by alkaline dehydrochlorination to produce glycidol or epichlorohydrin.

Moreover such new integrated process is able to produce a DCH according to original process WO2005/021476, using the MCH as a starting material according to the present modified process. The production rates of DCH and MCH respectively can be independently set according to the actual demand on ECH or glycidol production In another, preferred re-arrangement of such third hydrochlorination process embodiment of original process according to WO2005/021476 is to replace second vacuum distillation step for heavy undesired products removal by new vacuum distillation step, where dichloropropanol-rich fraction as a distillate is returned back to the reactor system, and the DCH and/or MCH pure product fraction as a side stream is further processed to the desired product with and heavy by-product fraction leaving the distillation step as a distillation residue are further processed.

The carboxylic acids or their derivatives used in the MCH or DCH synthesis can be either derived from the conventional petroleum based synthesis or, more preferably, from the bio-derived feedstock, such as acetic acid from bio-ethanol, succinic or adipic acid from glucose. Use of such bio-derived carboxylic acids enables a fully renewable carbon content of MCH/DCH feedstock and respective products from them to be achieved.

Subsequently, in all above described MCH process embodiments, the production ratio between epichlorohydrin from glycerine via DCH, and glycidol from glycerine via MCH, can be varied based on actual demand, which is a substantial advantage of present invention where the production rates of both intermediates MCH and DCH, and thus respectively both products glycidol GLD and epichlorohydrin ECH, are not fixed based on stoichiometry.

Ultimate care must be taken about the proper material selection of described hydrochlorination process to produce MCH. No ferric material is to be used, and it is advantageous to use enamel steel or fluoro-polymer lined steel or the solid fluoro-polymers or the combination thereof.

Another chlorohydrin feedstock can consist of chlorohydrin ethers of various alcohols or hydroxy-derivatives of aromatic hydrocarbons. In this case corresponding glycidylethers are produced with all environmental, economic and technical benefits.

Another chlorohydrin feedstock can consist of chlorohydrins which contain, apart from chlorine group, at least two hydroxy groups in the molecule. In this case corresponding epoxyalcohols are produced with all environmental, economic and technical benefits.

Alkaline Agent Feedstock:

The alkaline agent can be commonly known compound derived from hydroxides or carbonates of alkali metals or alkali-earth metals, in form of solution or suspension. Preferably, for purpose of pure salt recovery, the alkaline agent is sodium hydroxide, as a 16-52% w/w solution which is produced in all types of the NaCl electrolysis systems, e.g. membrane, diaphragm or mercury process.

Alkoxides are considered as suitable, but not preferable reactant, especially for the continuous process, due to corresponding ether formation during the dehydrochlorination.

As would be well understood by persons skilled in the art that it is important to ensure that the reactor vessels and connecting pipes, fittings, etc., are made from materials resistant to corrosion. The scope for corrosion is high and can arise from multiple sources, as the reaction mixtures at various stages in the continuous mode can be acidic or alkaline and/or contain high salt content, including presence of water.

Dealing with brine slurry can particularly lead to abrasive corrosion issues. Therefore, it is even possible that different corrosion resistant materials are needed at the various stages of the production system.

Special care must be taken about the material selection for distillation device for MCH recovery according to present invention. Neither carbon steel nor stainless steel is preferred selection. We found glass, glass-lined or fluoropolymer-lined equipments are very suitable for MCH recovery distillation device.

Reaction Step to Produce GLD:

Generally, the reaction conditions in the reaction zone are preferably between −10° C. to 100° C. The reaction temperature is more preferably between 0-80° C., even more preferably 10-60° C., and most preferably 20-40° C.

The mean residence time of the continuous operated reactor zone can be in range from 0.1 to 5 hours, more preferably 0.3 to 2 hours, most preferably 0.5 to 1 hour.

The specific feeding rate of alkaline agent, e.g. NaOH solution, expressed as kilograms of alkaline agent dry basis per hour per cubic meter of reaction volume, can be in range 5-5000 kg/hour/m$^3$, more preferably 25-1000 kg/hour/m$^3$, most preferably 125-500 kg/hour/m$^3$.

We also found the use of an organic solvent is not necessary for reaction itself, as it can be carried out in natural water environment with a very good yield. Water in this case comes from alkaline agent solution and from the reaction. Moreover, use of azeotropic agent or solvents in the reactor is not useful as the azeotropic agent/solvents increase the reactor volume and thus decrease the concentration of reactants resulting in lower reaction rates and more prolonged reaction times. Moreover due to presence of alkaline agent in the reaction step, taking into account it is well known catalyst of many reactions, like etherification, said use is not preferred as such reactions can occur and produce by-products like corresponding ethers of epoxides, e.g. glycidol and/or chlorohydrins, e.g. MCH. Thus the use of azeotropic agent/solvents at the first step should be minimal, except its in-situ generation by dehydrochlorination reaction.

The reactor and subsequent vessels are preferably made of materials which resist corrosion. Particular care must be taken about the distillation step material design as MCH and esters of carboxylic acid can cause a significant corrosion attack to the common carbon or stainless steels by the temperatures above 100° C.

The yield of initial glycidol in the preliminary dehydrochlorination step can be between 97-99%. Overall, the yield of the glycidol preparation in a continuous mode, including all separation and purification steps can be between 95-96%. Thus, the care taken in the choice of the azeotropic agent and in removal of any latent ionic species in the sub-zones ensures that the high yield of glycidol is achieved ultimately in a continuous manner.

Product Separation Steps:

The reaction mixture dehydration is an essential step for further processing of the glycidol-containing mixture.

The main purpose is to reduce the content of water in such mixture as much as possible to reduce the solubility of corresponding salt to an appropriate low level, so that the degradation pathways for the produced glycidol are minimized and the amount of produced salt is maximized. This is done by use of an appropriate azeotropic agent which allows the removal of water by the use of distillation, preferably operated under the reduced pressure in a pure rectification column arrangement, where reactor outlet is fed directly to the bottom of the column, i.e. to/above the boiler.

The second important purpose of adding of such azeotropic agent is to adjust the physical properties of the salt-epoxide, e.g. chloride salt-glycidol, slurry after water removal to be able to process it efficiently in the next steps, i.e. in filtration.

Thus, the reaction mixture containing glycidol, water, salt and very small amount of unreacted alkali is fed to the bottom of a vessel or boiler having a rectification vacuum column, and an appropriate amount of azeotropic agent is fed to the column, preferably to the column bottom, even more preferably to the boiler, most preferably together with the reaction mixture feed.

In the preferred embodiment the appropriate azeotropic agent forms two liquid phases as a distillate, where the water-rich phase is completely removed and water-poor phase is fully or partially refluxed back to the column.

Water rich phase from such dehydration step with some portion of dissolved azeotropic agent, which is further recovered by separated distillation in order to recover such azeotropic agent as a distillate to be recycled back to the dehydration step, and almost pure water as a distillation residue.

The dehydrated reaction mixture, in the form of slurry, consists of epoxide, e.g. glycidol, salt, unreacted chlorohydrin, e.g. MCH, and azeotropic agent, and leaves this dehydration step as a distillation residue.

Maximal temperature in the dehydration step should be in range of 0-100° C., more preferably 20-80° C., most preferably 40-60° C.

The pressure in the dehydration step should be reduced and should be set up with respect to the maximal temperature in such dehydration zone, to amount of azeotropic agent used and with respect to the dew point of the azeotropic mixture of such azeotropic agent with water. Such dew point should be in range of −5-50° C., more preferably 0-30° C., even more preferably 5-20° C., most preferably 10-15° C.

The selection of the azeotropic agent is vital for the success of the dehydration zone to work efficiently in a continuous process.

It is highly preferred that azeotropic agent partially or totally remains in the de-hydrated reaction mixture leaving the de-hydrating distillation column bottom, allowing adjustment of the properties of this mixture to allow its transport and further efficient processing in the filtration step. Moreover such azeotropic agents must be selected from those which enable precipitation of the salt crystals in a suitable form for efficient filtration and transportation, and does not form sticky slurry. Moreover, crystals of salt must be easily filtered, washed and dried on order to reduce content of TOC as much as possible.

The amount of azeotropic agent to be used should be sufficient to ensure the following parameters of de-hydrated mixture to be filtered:
- dehydration temperature range of 0-100° C., more preferable 20-80° C., most preferable 40-60° C.
- content of water in dehydrated step less than 10%, more preferable less than 5%, even more preferable less than 3%, most preferable less than 1%.
- to keep the concentration of dispersed salt in a pumpable/transportable range.
- to keep the concentration of glycidol on an appropriate level to ensure low reaction rate towards serial reaction product formation.

So that it has been found that the amount of azeotropic agent in the dehydrated mixture to be further filtered should be in range 20-80%, more preferably 25-70%, even more preferably 30-60%, most preferably 35-45%.

The dissolved salt content in dehydrated mixture should be lower than 5%, more preferable less than 1%, even more preferable less than 0.5%, most preferable less than 0.1%.

To ensure that the quality of the recovered salt is high, it is highly preferred that the azeotropic agent should be fully miscible with glycidol and partially miscible with water. A totally water miscible azeotropic agent is not preferred. We found that polar-type substituted hydrocarbons are useful in this regard.

Furthermore, to be able then to separate the azeotropic agent from the glycidol and to recover it from the water-rich phase (layer), the azeotropic agent has preferably a normal boiling point less than 150° C., more preferable less than 130° C., and does not form an azeotropic mixture with glycidol. This condition ensures economic recyclability of the azeotropic agent in the preferable continuous process.

Preferably, the azeotropic agent must be an inert or must be as low reactive, especially towards glycidol, under the process conditions as possible. To reduce its reactivity, the type of hydrocarbons, their structure and chemical properties must be taken into account.

The azeotropic agent is preferably selected also with respect to filtration efficiency, capability to efficiently wash the filter cake which consists of salt, e.g. NaCl, and organics, i.e. to remove epoxide, e.g. glycidol, based compounds almost completely and to efficiently dry the filter cake after flushing by means of common drying techniques. The ultimate desired purity of the salt is an essential feature of present invention and such good purity represented by low TOC is enabled by use of the carefully selected appropriate azeotropic agent.

It is also highly preferred to use low- or non-toxic compound with low or industry acceptable hazard properties.

Surprisingly, only a limited number of compounds meet all mentioned requirements. Thus there can be used various substituted or non-substituted hydrocarbons, such as, but not limited to, alcohols, ketones, epoxides, aliphatic hydrocarbons, aromatic or cyclic hydrocarbons, etc.

The more preferred group of azeotropic agent is aliphatic alcohols with primary, substituted primary or secondary or tertiary structure (non-substituted primary structure is preferred only in some special cases based on feedstock esters content), aliphatic ketones, aliphatic chlorinated hydrocarbons, aliphatic epoxides, aliphatic hydrocarbons and cyclic hydrocarbons. Low molecular weight versions having branched groups are preferred, to reduce any reactions with the glycidol.

The preferred agents in term of toxicity, cost, heterogeneous azeotropic mixture composition, recovery, safe handling, salt purity are n-butanol, iso-butanol, secondary butanol, methyl isobutyl ketone, n-heptane, dichloroethane, cyclohexane and epichlorohydrin.

The chlorohydrin feedstock, e.g. MCH with or without DCH, which were produced by hydrochlorination of glycerine using carboxylic acid as a catalyst, can contain some carboxylic acid and/or carboxylic acid esters. These carboxy-compounds can react, under the present process conditions, with produced glycidol directly or indirectly via liberated carboxylic acid to form corresponding glycidylesters, which can lower the quality of the product. It has been found, some aliphatic alcohols presented in the system can significantly lower the content of such glycidylesters in the glycidol product due to their ability, it is believed, to perform transesterification reaction, i.e. due to favourable chemical equilibrium to make corresponding esters of such aliphatic alcohols from other esters presented in the system, e.g. glycidylesters or esters of alcohols coming from feedstock. Thus, for example, glycidylacetate amount in the reaction dehydrated mixture can be significantly lowered by use of iso-butanol or n-butanol, which formed corresponding butylacetates, which are easily removed from product glycidol by distillation. This process according to this invention therefore gives an ester content in glycidol which is less than 1%, more preferably less than 0.1%, most preferably less than 0.01%. Thus, it is another advantage of usage of some aliphatic alcohols as an azeotropic agent. It is seen therefore that the aliphatic alcohols act as an azeotropic agent and efficiently lower the formation of glycidylesters under the conditions of present process.

As surprisingly found, one of the preferred azeotropic agents is epichlorohydrin. It can be added to the dehydration step in a standard way or it can be formed in-situ from dichloropropanol containing feedstock (see Scheme No. 11). It has been found, if the feedstock contains MCH and DCH (in an appropriate ratio), epichlorohydrin is then formed additionally due to the dehydrochlorination of DCH by means of alkaline agent. Thus, no other azeotropic agent is required to be added in the dehydration distillation step in this case. It was surprisingly found, that epichlorohydrin functions in the same way as iso-butanol or other described azeotropic agents.

ECH recovery from water distillate is also done by the same way in additional second distillation, where further recovered ECH is withdrawn as a ECH-rich liquid distillate phase with the content of the water less than 2.0%, to be optionally recycled back to the reactor or to the dehydrating step or to the final distillation.

We surprisingly found that only an appropriate MCH to DCH ratio can lead to efficient process with high yield, good quality of produced salt and suitable physical properties of de-hydrated mixture to be filtered. Thus, if the molar ratio MCH:DCH is equal or lower than 1:1, the yield of ECH does not go up and the yield of glycidol does not go down proportionally. Moreover, if the MCH:DCH ratio lies substantially below 0.8:1.2, then the physical properties of reaction mixture leaving the reactor and especially dehydrated mixture leaving the dehydration zone to be further filtered, are getting worse rapidly. Sticky slurry, which can plug all connected parts of technology by sticky solid phase is formed. The dehydration boiler, column, pipes, fitting are heavily fouled, even plugged.

The present inventors also found, surprisingly, the quality of produced dry salt is lower with content of TOC above 500 mg/kg.

The advantage of such embodiment with ECH acting as an azeotropic agent is that the full utilization of production volumes can be made and no other compounds need to be handled. This advantage requires the MCH to DCH ratio in feedstock to be above around 0.8:1.2. However, due to narrow boiling points, the separation between unreacted DCH to be recovered and produced glycidol is more demanding using distillation, especially in case of low ratio MCH to DCH in feedstock.

It can be seen therefore, that ECH is used as the standard azeotropic agent fed to the dehydration step and finally recovered in the same way as described for the other azeotropic agent, e.g. iso-butanol.

Thus, several issues should be taken into consideration to select optimal azeotropic agent to be used. For standalone production of glycidol without parallel production of epichlorohydrin, more preferred azeotropic agent is iso-butanol and methyl isobutyl ketone. In the case, significant amount of esters or/and carboxylic acids is present in feedstock MCH, more preferred azeotropic agents are iso-butanol and n-butanol. In the case, ECH should be produced in appropriate ratio to glycidol, no extra added different azeotropic agent is preferred and ECH acts as such azeotropic agent.

Bio derived alcohols, such as bio-derived iso-butanol and n-butanol can be also used. By the term "bio-derived" we mean compounds produced from green matter such as biomass.

Salt Filtration:

The reaction salt is produced in the form of a suspension/slurry in the de-hydrated mixture and has to be removed by filtration. Some of the salt is also dissolved in the reaction mixture. Thus, it is important to have a dehydration step performed to precipitate as much of the salt as possible.

The filtration step can be like those commonly known from state-of-the-art. The main features of such filtration consist of filtration itself, flushing of filter cake by use of the same compound as used as the azeotropic agent, which allows to recover it together and reduces the overall cost of process.

Finally, based on selected type of filtration and quality demand, the filter cake can be subject of drying by commonly known methods like direct drying (hot-gas atmospheric or vacuum drying), infrared-radiant drying or conducted drying, etc., from which the flushing medium can be recovered, e.g. by condensation. More preferred type is vacuum drying to avoid high temperatures during the salt drying and subsequently to allow some heat-sensitive molecules to be vaporized, not polymerized.

It was found that in the case of NaCl salt, the recovered salt by the standard filtration is sufficiently pure in terms of total organic content TOC for common market demand. In this case, salt contains less than 300 ppm TOC, more preferably less than 200 ppm of TOC, even more preferably less than 100 ppm of TOC.

For extremely high purity demand for the TOC content (e.g. for use in membrane type of electrolysis of the NaCl/KCl water solution), the salt can be further purified by common methods like crystallization, high-temperature treatment (oxidation) or wet oxidation of corresponding concentrated brines.

It was also found, after such dry salt dissolving in pure de-ionized water, the concentrated brine can be further treated by system of appropriate oxidation steps done by hydroxyl radicals formed by use of appropriate catalytic system and source of energy for radical formation, or done by hypochlorites by use of appropriate catalytic system, to reach the TOC content below the limits required by membrane type of electrolysis of NaCl or KCl, e.g. less than 10 ppm or less than 5 ppm.

Thus, this salt in both solid form or in form of brine can be further re-processed in a chlor-alkali electrolysis plant, diaphragm or membrane process, to produce corresponding alkali metal hydroxide for the first reaction step of present invention.

Thus the process of this invention is further both environmentally and operating-cost beneficial and efficient, as the salt removal and recovery is the essential feature of the process in order to achieve stable high yields of the glycidol and receiving the waste water not containing stoichiometric amount of salt from dehydrochlorination of MCH.

Glycidol Advanced Purification:

Glycidol is a nearly stable compound under defined conditions. However, any catalyst of polycondensation/polymerization and/or use of high temperature must be avoided.

The filtrate leaving the filtration step, even with low content of water, will still and always contain traces of ionic compounds such as unreacted alkaline reagent and dissolved salts. Some of those compounds are described in literature as polymerization/polycondensation catalysts. We have determined that even if traces of Na, Cl or OH species, e.g. in form of NaCl or NaOH, are present in filtrate, the further filtrate processing is not suitable due to significant polycondensation/polymerization reaction which decrease the overall glycidol yield.

One possible method to remove Na species is by use of cation exchange process, where the $Na^+$ ions are captured by an ion exchange resin. The $Cl^-$ ions from the ionic pair can be then either removed by anion exchange resin or $H^+C^-$ formed can further react with HCl acceptor, e.g. already present epoxide, e.g. glycidol, oxirane group back-forming the corresponding chlorohydrin, e.g. MCH. Although the cation exchange resin with HCl acceptor (e.g. glycidol) can reduce content of ionic species significantly, the efficiency is not sufficient to reduce them down to appropriate low level, moreover, glycidol yield goes down due to chemical unstability under such ion-exchange step conditions.

We determined that the only method to completely remove traces of the ionic compound from the filtrate, down to an appropriate level, and retain the very high yield of glycidol, i.e. with very low degree of glycidol degradation, was by using continuous short residence time vacuum evaporation, e.g. wiped-film system (see Scheme No. 7). Only this Operation Combines:
 a) the required separation efficiency for the removal of the ionic compounds,
 b) the necessary short residence time of epoxide, e.g. glycidol, to be present in the liquid phase during evaporation and
 c) maintains the appropriate low temperature in the evaporator so as not to exceed the appropriate level, where the epoxide, e.g. glycidol, and chlorohydrin, e.g. MCH, become subject of decomposition.

Thus the filtrate containing the undesired ionic compounds and solvent in form of azeotropic agent from previous step, is continuously fed to the vacuum operated thin-film evaporator, preferably rotating thin-film evaporator, and the epoxide, e.g. glycidol, unreacted chlorohydrin, e.g. MCH, and azeotropic agent leave the system as distillate, and the ionic compounds and small amount of polymeric compounds leave the system as distillation (evaporation) residue.

It is an essential feature of the present invention that an appropriate amount of azeotropic agent from the previous dehydration step should be in the processed filtrate, in order to ensure the appropriate low temperature of the distillation=evaporation is achieved and that there is low concentration of epoxide, e.g. glycidol, in the liquid-phase film in the continuously operated thin-film evaporator.

This is the most efficient method for complete removal of such ionic compounds.

Further, it is also advantageous to link the vapours from this evaporation method directly, without condensation, to the next distillation separation step, thus, saving the energy.

A suitable thin-film evaporator can be selected from all types of evaporators forming thin-film with a short residence time of liquid phase, e.g. falling-film evaporator, rotating-film evaporator. The most preferred type is the rotating-film evaporator, e.g. wiped-film type, which can handle solids precipitated from the liquid film after evaporation and sticky slurry formation on the heat-exchange surface.

Operating pressure can be selected in range from 0.1 to 50 torr, more preferred from 0.5 to 10 torr, the most preferred from 1 to 5 torr. With respect to glycidol and MCH unstability, the temperature of heating medium must be kept below 200° C., more preferred below 180° C., the most preferred below 160° C. in order to avoid too high wall temperature leading to glycidol degradation.

The composition of the vapours leaving the evaporator is almost the same as the filtrate continuously fed to the evaporator, minus the ionic species and some heavy polymeric compounds, which leave the evaporator as evaporation residue in form of highly viscous sticky slurry.

The content of the ionic species in the vapours or in respective condensate, primarily in the epoxide, e.g. glycidol, product with some azeotropic agent, some chlorohydrins, e.g. MCH, is less than 1000 ppm, preferably less than 100 ppm weight, more preferably less than 10 ppm weight and the most preferably less than 1 ppm weight.

Filtrate Separation Sub-Zone:

After traces of ionic compounds are removed, the filtrate can be efficiently processed/distilled in a vacuum distillation system. The ionic species content in the zone feed at this stage is less than 1000 ppm weight, preferably less than 100 ppm weight, more preferably less than 10 ppm weight and the most preferably less than 1 ppm weight.

At this stage, as there is virtually no catalyst left to promote unwanted glycidol degradation/polymerization/polycondensation in the feed mixture at this sub-zone, the glycidol is sufficiently stable under the conditions (temperature, residence time) of this final distillation step.

The distillation can be carried out batchwise (see Scheme No. 8) or continuously in system of one, two or three distillation columns (see Scheme No. 9), operated under reduced pressure depending on the required purity of glycidol and type of arrangement (batch, continuous). A system with low residence time and low pressure drop is preferred.

Generally, the azeotropic agent with traces of water leaves the system as a first distillate (dry azotropic agent can be optionally withdrawn as a side product or can be dried by another distillation), glycidol as a second distillate (also in form of side stream), unreacted chlorohydrins, e.g. MCH or MCH+DCH, as a third distillate (also in form of side stream), and undesired heavy polymeric polyol-based by-product as a distillation residue. This by-product can be further optionally used as a feedstock source for polyglycerine in resin and polymer chemistry.

It has been found that, in order to keep chemical stability of the whole system, the distillation of the glycidol should not be executed by the higher system pressure than the one, where the respective boiling point of glycidol is lower than 80° C., more preferably not more than 60° C., most preferably not more than 45° C. It is also essential the chlorohydrin, e.g. MCH, recovery distillation should not be executed by the higher system pressure than that one, where the respective boiling point of 3-chloro-1,2-propanediol is lower than 110° C., more preferably not more than 90° C., most preferably not more than 83° C.

More preferred system for the continuous vacuum distillations, involves a two column arrangement (see Scheme No. 10):
 a) the first vacuum distillation is dedicated for the recovery of the mixture of azeotropic agent with small trace of water and glycidol as distillate and,
 b) the crude glycidol containing unreacted MCH and undesired heavy polymeric by-products as distillation residue, is fed into a second distillation unit, where in the second vacuum distillation, pure glycidol is produced as distillate and unreacted MCH, to be recycled to the reaction, as a column side product.

Heavy by-products leave the second distillation as a bottom distillation residue and can be further used with or without treatment as a feedstock into other polymer chemistry as a source of polyols.

The recovered unreacted chlorohydrins, e.g. MCH, are recycled back to the reaction step, and the recovered azeotropic agent is recycled back to dehydration step.

From these processes, the glycidol that is produced, is of a very high quality. It has been found, that the glycidol purity is greater than 96.0% (which is guarantee of Sigma-Aldrich), more preferably greater than 99.0%, most preferably greater than 99.9%.

The impurities found in the glycidol produced by this process are largely non-halogenated esters and ethers, e.g. glycidylester and glycidylglycerolether. There are even minor amount of other organic compounds, e.g. halogenated or non-halogenated.

Preferably, the ester content in glycidol is less than 1%, more preferably less than 0.1%, most preferably less than 0.01%.

The halogenated hydrocarbons content in glycidol is less than 0.05%, more preferably less than 0.01%, most preferably less than 0.005%.

The high quality glycidol produced by this process starting from bio-derived glycerol has high renewable carbon content, which, in the best case, can be 100%.

From these processes, the epichlorohydrin that is produced is of a very high quality. It has been found that the epichlorohydrin purity is greater than 99.5%, more preferably greater than 99.7%, most preferably greater than 99.9%.

The high quality epichlorohydrin produced by this process starting from bio-derived glycerol has high renewable carbon content, which, in the best case, can be 100%.

Glycidol has become an important intermediate for the production of materials such as polyols, functional epoxides, polyesters such as alkyd resins, phosphate esters, which intermediates are then converted into useful surfactants, coatings, adhesives, lubricants. One of the big advantage of high purity glycidol use is extremely low, even zero, amount of chlorinated compounds, particularly chlorohydrins, which eventually may result in high residual chlorine, e.g. so called "total hydrolyzed chlorine", content in final application molecules.

The other advantage of epoxides, e.g. glycidol or epichlorohydrin, manufactured according to the present invention, is its high renewable carbon content, if the starting glycerol for the production of chlorohydrins has a natural origin. It allows to use such epoxides as a starting material for applications with high renewable carbon content.

Glycidol is particularly useful starting material for hyperbranched polyols manufacturing, preferably polyetherpolyols, by means or various catalytic systems. Even if the hyperbranched polyether polyols contain ethereal bonds, no etherification water is formed during preparation from glycidol. Thus, the reaction can be easily controlled and completed towards extremely low content of epoxy groups.

Glycidol as a starting material of such polyetherpolyols can be combined with other type of epoxyalcohols or other hydroxy-derivatives, e.g. alcohols or aromatic hydroxy-derivatives, to control the hyperbranched structure and its properties.

Functional epoxides are made, for example 2,3-epoxypropyl chloroformate. Reaction of glycidol with isocyanates affords the commercially important glycidyl urethanes. Glycidol is used as an intermediate in the production of pharmaceuticals, as an additive for synthetic hydraulic fluids and as a reactive diluent in some epoxy resin systems. It is a stabilizer for natural oils and vinyl polymers, a dye-levelling agent and a demulsifier.

Such a high quality and more efficiently produced glycidol enables a greater range of downstream applications, such as:

High solid and waterborne air drying and baking alkyds for coating on wood and metal.

Polyesterpolyols, polyether polyols as reactive oligomers or plasticizers or flexibilizers, surfactants, further components for PUR foams, coatings, casting resins and adhesives.

Flame retardants with functional group enabling their incorporation into the polymeric structures.

Glycidylmethacrylate from methylmethacrylate.

The ECH produced by the processes described herein is of particular high purity and has high renewable carbon content.

The ECH produced by the processes described in this invention is useful in manufacture of a vast range of epoxy derivatives such as epoxy resins, glycidyl ethers, glycidyl esters, glycidyl amides and imides.

These resins are used as such or are formulated further with various additives (e.g. pigments, fibres, coating aids, etc.) to make application products, which are cured/dried to make the final plastics, e.g. coatings, paints, adhesives, films, which will be used in food and drink applications where the final plastic is in contact with human food, industrial tooling and composites, electrical systems and electronics, consumer, sports and marine applications, and aerospace and wind turbine applications.

Further, other applications are as coagulants and wet-strength resins, as cationization agents, as flame retardants, as products which will be used as detergent ingredients, and are epichlorohydrin elastomers for rubber type applications.

Epoxy resins give engineering quality plastics with high durability, and stability under extreme conditions, including outdoor and space conditions.

In particular these downstream applications have high content of renewable carbon. The term "Renewable carbon" is defined as being derived from biomass instead of previous fossil-based products. This renewable carbon content is measured in terms $C^{14}$ isotope content according to respective codes.

| Legend to the Attached Schemes: | | | |
|---|---|---|---|
| Equip. ID | Description | Stream ID | Description |
| Scheme No. 1 | | | |
| 1 | Dehydrochlorination reaction zone | 50 | Chlorohydrin inlet |
| 2 | Dehydration zone | 51 | Alkaline agent inlet |
| 3 | Distillation column | 52 | Reaction mixture |
| 4 | Condenser | 53 | Azeotropic agent inlet |
| 5 | Liquid-liquid separator | 57 | Water from dehydration |
| 6 | Filtration zone | 58 | Dehydrated reaction mixture |

-continued

| Legend to the Attached Schemes: | | | |
|---|---|---|---|
| Equip. ID | Description | Stream ID | Description |
| 7 | Short residence time evaporation zone | 59 | Washing azeotropic agent |
| 8 | Condenser | 60 | Wet salt |
| 9 | First azeotropic agent distillation column | 61 | Filtrate |
| 10 | Condenser | 62 | Residual ionic species |
| 11 | Reflux separator | 64 | Ionic species free filtrate |
| 12 | Reboiler | 68 | Azotropic agent to be recycled |
| 13 | Second epoxide distillation column | 69 | Crude epoxide |
| 14 | Condenser | 73 | Distilled product epoxide |
| 15 | Reflux separator | 74 | Crude chlorohydrin |
| 16 | Reboiler | 78 | Chlorohydrin to be recycled |
| 17 | Third chlorohydrin distillation column | 79 | Heavy by-products |
| 18 | Condenser | 83 | Azeotropic agent to be recycled |
| 19 | Reflux separator | 84 | Waste water |
| 20 | Reboiler | | |
| 21 | Azeotropic agent recovery column | | |
| 22 | Condenser | | |
| 23 | Reflux separator | | |
| 24 | Reboiler | | |
| Scheme No. 2 | | | |
| 2 | Reaction + dehydration zone | 51 | Chlorohydrin inlet |
| 3 | Distillation column | 52 | Alkaline agent inlet |
| 4 | Condenser | 53 | Azeotropic agent inlet |
| 5 | Liquid-liquid separator | 57 | Water from dehydration |
| 6 | Filtration zone | 58 | Dehydrated reaction mixture |
| 7 | Short residence time evaporation zone | 59 | Washing azeotropic agent |
| 8 | Condenser | 60 | Wet salt |
| 9 | Batch distillation boiler | 61 | Filtrate |
| 10 | Batch distillation column | 62 | Residual ionic species |
| 11 | Condenser | 64 | Ionic species free filtrate |
| 12 | Reflux separator | 68.1 | Water fraction to be recycled |
| 13 | Azeotropic agent recovery distillation boiler | 68.2 | Azeotropic agent fraction to be recycled |
| 14 | Azeotropic agent recovery column | 68.3 | Epoxide fraction as product |
| 15 | Condenser | 68.4 | Chlorohydrin fraction to be recycled |
| 16 | Reflux separator | 69 | Heavy by-products |
| | | 73 | Azeotropic agent to be recycled |
| | | 74 | Waste water |
| Scheme No. 3 | | | |
| 1 | Dehydrochlorination reaction zone | 50 | Chlorohydrin inlet |
| 2 | Dehydration zone | 51 | Alkaline agent inlet |
| 3 | Distillation column | 52 | Reaction mixture |
| 4 | Condenser | 53 | Azeotropic agent inlet |
| 5 | Liquid-liquid separator | 57 | Water from dehydration |
| | | 58 | Dehydrated reaction mixture |
| Scheme No. 4 | | | |
| 2 | Reaction + dehydration zone | 51 | Chlorohydrin inlet |
| 3 | Distillation column | 52 | Alkaline agent inlet |
| 4 | Condenser | 53 | Azeotropic agent inlet |
| 5 | Liquid-liquid separator | 57 | Water from dehydration |
| | | 58 | Dehydrated reaction mixture |
| Scheme No. 5 | | | |
| 2 | Dehydration zone | 50 | Chlorohydrin inlet |
| 3 | Distillation column | 51 | Alkaline agent inlet |
| 4 | Condenser | 52 | Reaction mixture |
| 5 | Liquid-liquid separator | 53 | Azeotropic agent inlet |
| 24 | Chlorohydrin cooler | 57 | Water from dehydration |
| 25 | NaOH cooler | 58 | Dehydrated reaction mixture |
| 26 | Dehydrochlorination reaction zone | | |
| Scheme No. 6 | | | |
| 2 | Dehydration zone | 50 | Chlorohydrin inlet |
| 3 | Distillation column | 51 | Alkaline agent inlet |
| 4 | Condenser | 52 | Reaction mixture |
| 5 | Liquid-liquid separator | 53 | Azeotropic agent inlet |
| 24 | Chlorohydrin cooler | 57 | Water from dehydration |
| 25 | NaOH cooler | 58 | Dehydrated reaction mixture |
| 27 | Dehydrochlorination reaction zone | | |

| Legend to the Attached Schemes: | | | |
|---|---|---|---|
| Equip. ID | Description | Stream ID | Description |
| Scheme No. 7 | | | |
| 7 | Short residence time evaporation zone | 61 | Filtrate |
| 8 | Condenser | 62 | Residual ionic species |
| | | 64 | Ionic species free filtrate after distillation |
| Scheme No. 8 | | | |
| 9 | Batch distillation boiler | 64 | Ionic species free filtrate |
| 10 | Batch distillation column | 68.1 | Water fraction to be recycled |
| 11 | Condenser | 68.2 | Azeotropic agent fraction to be recycled |
| 12 | Reflux separator | 68.3 | Epoxide product fraction |
| | | 68.4 | Chlorohydrin fraction to be recycled |
| | | 69 | Heavy by-products |
| Scheme No. 9 | | | |
| 9 | First azeotropic agent distillation column | 64 | Ionic species free filtrate |
| 10 | Condenser | 68 | Azeotropic agent to be recycled |
| 11 | Reflux separator | 69 | Crude epoxide |
| 12 | Reboiler | 73 | Distilled product epoxide |
| 13 | Second epoxide distillation column | 74 | Crude chlorohydrin |
| 14 | Condenser | 78 | Chlorohydrin to be recycled |
| 15 | Reflux separator | 79 | Heavy by-products |
| 16 | Reboiler | | |
| 17 | Third chlorohydrin distillation column | | |
| 18 | Condenser | | |
| 19 | Reflux separator | | |
| 20 | Reboiler | | |
| Scheme No. 10 | | | |
| 9 | First azeotropic agent distillation column | 64 | Ionic species free filtrate |
| 10 | Condenser | 68 | Azeotropic agent to be recycled |
| 11 | Reflux separator | 69 | Crude epoxide |
| 12 | Reboiler | 73 | Distilled product epoxide |
| 13 | Second epoxide distillation column | 74 | Heavy by-products |
| 14 | Condenser | 76 | Chlorohydrin to be recycled |
| 15 | Reflux separator | | |
| 16 | Reboiler | | |
| 25 | Side stream condenser | | |
| Scheme No. 11 | | | |
| 1 | Dehydrochlorination reaction zone | 50 | Chlorohydrins inlet |
| 2 | Dehydration zone | 51 | Alkaline agent inlet |
| 3 | Distillation column | 52 | Reaction mixture |
| 4 | Condenser | 57 | Water from dehydration |
| 5 | Liquid-liquid separator | 58 | Dehydrated reaction mixture |

EXAMPLES

2-Stage Dehydrochlorinating Reaction Under Different Molar Ratio NaOH vs. 3-Chloropropanediol (3MCH)

Example 1

233.5 g/h of 3-chloropropanediol with purity of 96.63% and 119.0 g/h (grams per hour) of sodium hydroxide aqueous solution with concentration of 49.77% were fed continuously into a first reactor of the production cascade. The five-neck glass reactor was equipped with a glass stirrer, thermometer, 3-chloropropanediol inlet, sodium hydroxide solution inlet, product outlet and was situated in a bath filled with cold water. The molar ratio between sodium hydroxide and 3-chloropropanediol was 0.726.

The reaction mixture with residual alkalinity was transferred under control mode by vacuum into a second reactor. The five-neck glass reactor was equipped with a glass stirrer, thermometer, reaction mixture inlet, azeotropic agent inlet, and product overflow and was situated in a heating bath filled with hot water. The reactor was fitted with distilling equipment for azeotropic removal of reaction water. The reaction water in amount of 93.5 ml/h (milliliters per hour) was removed by azeotropic vacuum distillation with 110.7 g/h of iso-butanol (iso-BuOH), which was fed into the reactor continuously. The mixture of reaction products with water content lower than 3% was collected in round-bottom flask situated in a cooling bath filled with water-ice mixture. Further portion of azeotropic agent trapped by deep cooling of exhaust gas from the distilling equipment was 6.2 g/h of iso-butanol and water.

346.9 g/h of the collected product was then filtered and the filter cake was washed by means of 36.2 g/h of iso-butanol to give 90.1 g/h of wet sodium chloride to be further dried, while the filtrate and the washing fluid were combined to give 290.2 g/h and analyzed by GC. The molar yield of glycidol based on the molar amount of 3-chloropropanediol converted was calculated.

The Basic Parameters and Results are Illustrated in the Following Table:

| | |
|---|---|
| Temperature in the dehydrochlorinating reactor | 18-21° C. |
| Temperature in the dehydrating reactor | 32-36° C. |
| Pressure in the dehydrating reactor | 2.5 kPa |
| Molar ratio of sodium hydroxide vs. 3-chloropropanediol | 0.726 |
| Yield of glycidol (mol/mol of 3-chloropropanediol converted) | 97.92% |

Undefined loss 19.4 g/h (3.88%)

Example 2

In the experimental unit according to Example 1, 224.0 g/h of 3-chloropropanediol with purity of 96.57% and 125.5 g/h of sodium hydroxide aqueous solution with concentration of 49.60% were reacted. The molar ratio between sodium hydroxide and 3-chloropropanediol was 0.795. The reaction mixture with residual alkalinity was transferred into the second reactor. The reaction water in amount of 85.0 ml/h was removed by azeotropic vacuum distillation with 144.9 g/h of iso-butanol and the mixture of reaction products with water content lower than 3% was collected. By deep cooling of exhaust gas 10.8 g/h of iso-butanol and water was trapped. 380.2 g/h of the collected product was then filtered and the filter cake was washed by means of 40.3 g/h of iso-butanol to give 86.5 g/h of wet sodium chloride to be further dried, while the filtrate and the washing fluid were combined to give 328.7 g/h and analyzed by GC. The molar yield of glycidol based on 3-chloropropanediol converted was calculated.
The Basic Parameters and Results are Illustrated in the Following Table:

| | |
|---|---|
| Temperature in the dehydrochlorinating reactor | 20-21° C. |
| Temperature in the dehydrating reactor | 33-36° C. |
| Pressure in the dehydrating reactor | 2.7 kPa |
| Molar ratio of sodium hydroxide vs. 3-chloropropanediol | 0.795 |
| Yield of glycidol (mol/mol of 3-chloropropanediol converted) | 97.66% |

Undefined loss 23.7 g/h (4.43%)

Example 3

In the experimental unit according to Example 1, 208.5 g/h of 3-chloropropanediol with purity of 96.57% and 132.5 g/h of sodium hydroxide aqueous solution with concentration of 49.60% were reacted. The molar ratio between sodium hydroxide and 3-chloropropanediol was 0.902. The reaction mixture with residual alkalinity was transferred into the second reactor. The reaction water in amount of 89.0 ml/h was removed by azeotropic vacuum distillation with 144.9 g/h of iso-butanol and the mixture of reaction products with water content lower than 3% was collected. By deep cooling of exhaust gas 4.1 g/h of iso-butanol and water was trapped. 395.9 g/h of the collected product was then filtered and the filter cake was washed by means of 40.3 g/h of iso-butanol to give 100.0 g/h of wet sodium chloride to be further dried, while the filtrate and the washing fluid were combined to give 331.0 g/h and analyzed by GC. The molar yield of glycidol based on 3-chloropropanediol converted was calculated.
The Basic Parameters and Results are Illustrated in the Following Table:

| | |
|---|---|
| Temperature in the dehydrochlorinating reactor | 19-21° C. |
| Temperature in the dehydrating reactor | 29-34° C. |
| Pressure in the dehydrating reactor | 2.7 kPa |
| Molar ratio of sodium hydroxide vs. 3-chloropropanediol | 0.902 |
| Molar yield of glycidol | 96.31% |

Undefined loss 2.1 g/h (0.40%)

Example 4

In the experimental unit according to Example 1, 205.5 g/h of 3-chloropropanediol with purity of 96.72% and 144.0 g/h of sodium hydroxide aqueous solution with concentration of 49.52% were reacted. The molar ratio between sodium hydroxide and 3-chloropropanediol was 0.991. The reaction mixture with residual alkalinity was transferred into the second reactor. The reaction water in amount of 87.5 ml/h was removed by azeotropic vacuum distillation with 181.1 g/h of iso-butanol and the mixture of reaction products with water content lower than 5% was collected. By deep cooling of exhaust gas 10.1 g/h of iso-butanol and water was trapped. 413.5 g/h of the collected product was then filtered and the filter cake was washed by means of 40.3 g/h of iso-butanol to give 107.7 g/h of wet sodium chloride to be further dried, while the filtrate and the washing fluid were combined to give 343.2 g/h and analyzed by GC. The molar yield of glycidol based on 3-chloropropanediol converted was calculated.
The Basic Parameters and Results are Illustrated in the Following Table:

| | |
|---|---|
| Temperature in the dehydrochlorinating reactor | 19-21° C. |
| Temperature in the dehydrating reactor | 28-34° C. |
| Pressure in the dehydrating reactor | 2.5-2.8 kPa |
| Molar ratio of sodium hydroxide vs. 3-chloropropanediol | 0.991 |
| Yield of glycidol (mol/mol of 3-chloropropanediol converted) | 93.26% |

Undefined loss 22.4 g/h (3.92%)
Comparison of Increased Molar Ratio Influence on Yield is Given in the Following Table:

| | Example 1 | Example 2 | Example 3 | Example 4 |
|---|---|---|---|---|
| Molar ratio NaOH:3-MCH | 0.726 | 0.795 | 0.902 | 0.991 |
| Yield of glycidol % | 97.92 | 97.66 | 96.31 | 93.26 |
| TOC in dry salt in mg/kg | 250 | 251 | 271 | 273 |

It is obvious from this sequence of experiments that the optimum of NaOH to 3-chloropropanediol molar ratios for glycidol preparation is located between approximately 0.80 and 0.95, when the yield of the glycidol is still high enough and the level of side products in the reaction mixture is low.
Dehydrochlorinating Reaction and Water Removal (Dehydration) in One Reaction Step

Example 5

In this example, the experiment was carried out at once only in the second stage equipment. The five-neck glass reactor was equipped with a glass stirrer, thermometer, 3-chloropropanediol-iso-butanol solution inlet, sodium hydroxide solution inlet, product overflow and was situated in a heating bath filled with hot water. The reactor was fitted with distilling equipment for azeotropic removal of reaction water under vacuum. In this reactor, 282.0 g/h of 3-chloropropanediol solution in iso-butanol with concentration of 3-chloropropanediol 33.16% and 65.5 g/h of sodium hydroxide aqueous solution with concentration of 49.46% were reacted. The molar ratio between sodium hydroxide and 3-chloropropanediol was 0.957. The reaction water in amount of 35.0 ml/h was removed by azeotropic distillation and the reaction mixture having residual alkalinity was collected. By deep cooling of exhaust gas 23.9 g of iso-butanol and water was trapped. 287.9 g/h of the collected product was then filtered and the filter cake was washed by means of 24.1 g/h of iso-butanol to give 47.1 g/h of wet sodium chloride to be further dried, while the filtrate and the washing fluid were combined to give 258.5 g/h and analyzed by GC. The molar yield of glycidol based on 3-chloropropanediol converted was calculated.

The Basic Parameters and Results are Illustrated in the Following Table:

| | |
|---|---|
| Temperature in the dehydrochlorinating and dehydrating reactor | 19-20° C. |
| Pressure in the reactor | 1.2-1.7 kPa |
| Molar ratio of sodium hydroxide vs. 3-chloropropanediol | 0.957 |
| Yield of glycidol (mol/mol of 3-chloropropanediol converted) | 92.46% |

Undefined loss 7.1 g/h (1.91%)

Comparison of One-Step and Two-Step Process is Given in the Following Table:

| | Example 3 | Example 5 |
|---|---|---|
| Dehydration carried out separately to main reaction | Yes | No |
| Molar ratio of NaOH vs. 3-chloropropanediol | 0.902 | 0.957 |
| Yield of glycidol in % | 96.31 | 92.46 |
| TOC in dry salt in mg/kg | 271 | 360 |

The Table shows that it is advantageous to split the glycidol preparation/reaction into two separated process steps (3-chloropropanediol reaction respectively reaction completion and dehydration) in order to reduce unwanted reactions of glycidol (i.e. condensation, hydration), to increase the glycidol yield and to increase a salt quality.

Reaction Water Removal with or without Azeotropic Agent

Example 6

In the experimental unit according to Example 1, 230.0 g/h of 3-chloropropanediol with purity of 96.72% and 131.5 g/h of sodium hydroxide aqueous solution with concentration of 49.27% were reacted. The molar ratio between sodium hydroxide and 3-chloropropanediol was 0.805. The reaction mixture with residual alkalinity was transferred into the second reactor. The reaction water in amount of 80.0 ml/h was removed by azeotropic vacuum distillation with 161.0 g/h of iso-butanol and the mixture of reaction products with water content lower than 2.5% was collected. By deep cooling of exhaust gas 2.5 g/h of iso-butanol and water was trapped. 428.0 g/h of the collected product was then filtered and the filter cake was washed with 40.3 g/h of iso-butanol to give 108.1 g/h of wet sodium chloride to be further dried, while the filtrate and the washing fluid were combined to give 356.7 g/h and analyzed by GC. The yield of glycidol based on 3-chloropropanediol converted was calculated.

The Basic Parameters and Results are Illustrated in the Following Table:

| | |
|---|---|
| Temperature in the dehydrochlorinating reactor | 20-21° C. |
| Temperature in the dehydrating reactor | 48-53° C. |
| Pressure in the dehydrating reactor | 6.7-7.2 kPa |
| Molar ratio of sodium hydroxide vs. 3-chloropropanediol | 0.805 |
| Yield of glycidol (mol/mol of 3-chloropropanediol converted) | 96.84% |
| TOC in dry salt | 217 mg/kg |

Undefined loss 15.5 g/h (2.75%)

Example 7

In the experimental unit according to Example 1, 228.5 g/h of 3-chloropropanediol with purity of 96.72% and 131.0 g/h of sodium hydroxide aqueous solution with concentration of 49.27% were reacted. The molar ratio between sodium hydroxide and 3-chloropropanediol was 0.807. The reaction mixture with residual alkalinity was transferred into the second reactor. The reaction water in amount of 80.0 ml/h was removed by vacuum distillation without azeotropically acting agent and the mixture of reaction products with water content lower than 1.5% was collected. By deep cooling of exhaust gas 12.8 g/h of water was trapped. 254.5 g/h of the collected product was then filtered to give 105.7 g/h of crude filter cake and 149.0 g/h of filtrate, which was analyzed by GC.

334.4 g of collected crude filter cake was mixed with 295.2 g of iso-butanol, filtered and the filter cake was rinsed with further part 120.8 g of iso-butanol to give 314.3 g of wet sodium chloride to be further dried, while both parts of the washing fluid were combined to give 422.3 g and analyzed by GC. The yield of glycidol based on 3-chloropropanediol converted was calculated.

The Basic Parameters and Results are Illustrated in the Following Table:

| | |
|---|---|
| Temperature in the dehydrochlorinating reactor | 19-21° C. |
| Temperature in the dehydrating reactor | 51-69° C. |
| Pressure in the dehydrating reactor | 0.93-1.20 kPa |
| Molar ratio of sodium hydroxide vs. 3-chloropropanediol | 0.807 |
| Yield of glycidol (mol/mol of 3-chloropropanediol converted) | 83.09% |
| TOC in dry salt | 470 mg/kg |

Undefined loss 12.0 g/h (3.34%)

Comparison of Use and Non-Use of Azeotropic Agent for Dehydration is Given in the Following Table:

| | Example 6 | Example 7 |
|---|---|---|
| Azeotropic agent usage for water removal | Yes | No |
| Molar ratio of sodium hydroxide vs. 3-chloropropanediol | 0.805 | 0.807 |
| Yield of glycidol (mol/mol of 3-chloropropanediol converted) | 96.84 | 83.09 |

|  | Example 6 | Example 7 |
| --- | --- | --- |
| Glycidol content in reaction water in % | 0.18 | 11.87 |
| Yield of glycidol including glycidol in distilled reaction water | 96.96 | 91.19 |
| TOC in dry salt in mg/kg | 217 | 470 |

The comparison table above clearly shows the benefit of using an azeotropic agent for reaction mixture dehydration. The main advantages are higher separation efficiency by lower system temperatures (glycidol stability issue), higher yield of glycidol and higher purity of salt to be further processed in downstream technologies. Moreover in case of no azeotropic agent use, the filter cake washing medium must be used anyway so that the additional washing azeotropic agent handling+treatment will be required. In present invention the azeotropic agent is also used as the filter washing medium, so no additional special azeotropic agent handling/treatment is required.

Glycidol Distillation without or with Ionic Species Removal Before

Example 8

From 1352.6 g of the filtrate, obtained by dehydrochlorinating of 3-chloropropanediol and filtration with glycidol content 30.88% and sodium chloride content 0.79 mg NaCl/g, rest of reaction water and iso-butanol were removed by two-step batch vacuum distillation under nitrogen. The distillation was performed in distilling equipment consisted of three-neck round-bottom distillation flask equipped with a thermometer, nitrogen inlet, packed column, distilling head with reflux and condenser. The distillation flask was immersed in the heating bath filled with heating oil. In the first step, first fraction of 55.4 g of water-iso-butanol mixture was collected. In the second step, the second fraction of 704.4 g of substantially dry iso-butanol containing 1.0% of glycidol was collected and crude glycidol as a distillation residue rich in glycidol was obtained. By deep cooling of exhaust gas 99.9 g of iso-butanol and water was trapped. In the last third step, the crude glycidol was fractionally distilled batchwise by means of rotating vacuum evaporator. 369.9 g of glycidol with purity of 98.70% was obtained, while the distillation residue after fractionation was 105.9 g, with glycidol content 1.02%. The recovered iso-butanol with glycidol was reused in dehydration step The yield of glycidol product distilled based on glycidol fed was 87.41% respectively 89.17% including the glycidol in iso-butanol recycled back to the dehydration step.

Example 9

The filtrate obtained by dehydrochlorinating of 3-chloropropanediol and filtration was purified from ionic species using rotating vacuum evaporator. The filtrate was continuously fed into the rotating evaporator, to give ionic species-free distillate with sodium chloride content lower than detection limit for argentometric titration and caustic soda content below the limit of acidometric titration. The mixture of 1826.8 g of the ionic species-free distillate containing 22.30% of glycidol and iso-butanol with low content of water was subjected to two-step batch vacuum distillation under nitrogen. The distillation was performed in distilling equipment according to Example 8. In the first step, the first fraction of 188.6 g of water-iso-butanol mixture was collected. In the second step, the second fraction of 1114.2 g of recovered iso-butanol containing 0.9% of glycidol was collected and crude glycidol as a distillation residue rich in glycidol was obtained. By deep cooling of exhaust gas 111.4 g of iso-butanol and water was trapped.

Then, in the last third step, the crude glycidol was fractionally distilled batchwise by means of rotating vacuum evaporator. 385.7 g of glycidol with purity of 98.49% was obtained, while the distillation residue after fractionation was 17.5 g. The recovered iso-butanol with glycidol was reused in dehydration step The yield of glycidol product distilled based on glycidol fed was 93.26% respectively 95.81% including the glycidol in iso-butanol recycled back to the dehydration step.

Comparison of Distillation Yield with and without Ionic Species Removal Before is Given in the Following Table:

|  | Example 8 | Example 9 |
| --- | --- | --- |
| Ionic species removal before distillation | No | Yes |
| Yield of glycidol in % (mol/mol in feed) | 87.41 | 93.27 |
| Yield of glycidol in % including the recycled glycidol in isobutanol | 89.17 | 95.81 |
| Purity of glycidol product in % wt. | 98.70 | 98.49 |

The table shows that without ionic species removal before distillation, the yield of glycidol fractionated in relation to glycidol in feed was lower than 90%. In contradiction with ionic species removal before distillation, the yield of glycidol fractionated in relation to glycidol in feed is higher than 95%. For better glycidol purity the distillation column should be used instead of evaporator.

Advantageous Arrangement of the Glycidol Preparation

Example 10

Step (a)+(b)+(c)—Reaction, Dehydration, Filtration

In the experimental unit according to Example 1, 1365 g of 3-chloropropanediol with purity of 96.72% and 770 g of sodium hydroxide aqueous solution with concentration of 49.27% were continuously fed into the first reaction step under the steady state conditions during the period of six hours. The molar ratio between sodium hydroxide and 3-chloropropanediol was 0.795. The reaction mixture with alkalinity 0.23 mg NaOH/g was transferred into the second reactor. The reaction water in amount of 560 ml was removed by azeotropic vacuum distillation by use of 945.9 g of iso-butanol continuously fed into the second reaction step—dehydration and the mixture of reaction products with water content 2.01% was collected. By deep cooling of exhaust gas 2.0 g of iso-butanol and water was trapped. Then 2483.1 g of the collected dehydrated reaction mixture was filtered and the filter cake was washed by means of 241.5 g of iso-butanol to give 662.7 g of wet sodium chloride to be further dried, while the filtrate and the washing fluid were combined to give 2061.7 g with content of glycidol 32.13 weight %, analyzed by GC. The yield of glycidol based on 3-chloropropanediol converted was calculated.

The Basic Parameters and Results of Step (a)+(b)+(c) are Illustrated in the Following Table:

| Temperature in the dehydrochlorinating reactor | 20° C. |
| --- | --- |
| Temperature in the dehydrating reactor | 48-54° C. |
| Pressure in the dehydrating reactor | 6.8-7.2 kPa |
| Molar ratio of sodium hydroxide vs. 3-chloropropanediol | 0.795 |

| | |
|---|---|
| Yield of glycidol (mol/mol of 3-chloropropanediol converted) | 97.66% |
| TOC in dry salt in mg/kg | 208 |

Undefined loss 36.0 g (1.08%)

Step (d1)—Ionic Species Removal

The rest of dissolved ionic species from the filtrate was removed in the rotating vacuum evaporator. 2061.7 g of the filtrate with glycidol content of 32.13 (14.96 MCH) % was continuously fed into the rotating evaporator and evaporated in the course of 8 hours to give 1959.7 g of distilled liquor with the glycidol content of 33.45 (13.44 MCH) %, while the paste like waste rest from the evaporator containing 40.57% of sodium chloride was 24.0 g. A small amount of water (ca 5 ml) was used to remove solid salt from the feed inlet during the process. By deep cooling of exhaust gas 72.5 g of iso-butanol and water was trapped.

The Basic Parameters and Results of Step (d1) are Illustrated in the Following Table:

| | |
|---|---|
| Temperature in the evaporator heating bath | 157-158° C. |
| Pressure in the evaporator | 0.27-0.53 kPa |
| Yield of glycidol (mol/mol in feed) | 98.99% |

Undefined loss 10.5 g (0.51%)

Step (d2)—Glycidol Distillation

Pure glycidol was obtained by three-step fractional vacuum distillation of 1959.7 g aforesaid liquor with the glycidol content of 33.45 weight %. The batch distillation was performed in distilling equipment according to Example 8 under nitrogen blanketing and three distilled fractions were obtained. In the first step, 57.2 g of water-iso-butanol mixture was collected as the first fraction. In the second step, 865.0 g of iso-butanol containing 0.2% of water was collected as the second fraction. Both of those fractions can be recycled back to the dehydration step. In the third step, 644.8 g of substantially pure glycidol with purity of 99.67 weight % was collected as a third fraction. 318.9 g of the distillation residue with glycidol content 0.32% and 3-chloropropanediol content 79.91% was recycled to the first reactor for next dehydrochlorination. By deep cooling of exhaust gas 49.8 g of iso-butanol and water was trapped.

The Basic Parameters and Results of Step (d2) are Illustrated in the Following Table:

| | |
|---|---|
| Temperature of boiler content | 35-112° C. |
| Vapour temperature (distilling head) | 21-45° C. |
| Pressure in the vapour output | 1.9-0.3 kPa |
| Yield of glycidol (mol/mol in feed, pure product only) | 98.04% |
| Yield of glycidol (mol/mol in feed, pure product including back recycled glycidol) | 98.81% |

Undefined loss 24.0 g (1.22%)

Advantageous Arrangement Result Summary (all Steps Together):

| | |
|---|---|
| Overall yield of glycidol (mol/mol of 3-chloropropanediol converted) | 94.78% |
| Overall yield of glycidol (mol/mol of 3-chloropropanediol converted) including glycidol to be recycled back to the reaction | 95.52% |
| Glycidol purity reached | 99.67 weight % |
| Content of glycidylglycerylolether + isobutylglycerylether | 300 ppm |
| Content of monochlorhydrine | 40 ppm |
| TOC in dry salt in mg/kg | 208 |

From above it is obvious the high efficient process for glycidol synthesis was developed. Glycidol purity obtained from such process was 99.67%, which is much more than the quality 96.0% available by Sigma-Aldrich, 2012. The quality of salt was sufficiently high to be further treated and recovered back to chlor-alkali electrolysis, e.g. diaphragm or membrane process, or to be sold on the market.

Reaction Water Removal with Different Azeotropic Agents

Example 11

In the experimental unit according to Example 1, 230.0 g/h of 3-chloropropanediol with purity of 96.72% and 131.5 g/h of sodium hydroxide aqueous solution with concentration of 49.27% were reacted. The molar ratio between sodium hydroxide and 3-chloropropanediol was 0.805. The reaction mixture with residual alkalinity was transferred into the second reactor. The reaction water in amount of 80.0 ml/h was removed by azeotropic vacuum distillation with 161.0 g/h of iso-butanol and the mixture of reaction products with water content lower than 2.5% was collected. By deep cooling of exhaust gas 2.5 g/h of iso-butanol and water was trapped. 428.0 g/h of the collected product was then filtered and the filter cake was washed with 40.3 g/h of iso-butanol to give 108.1 g/h of wet sodium chloride to be further dried, while the filtrate and the washing fluid were combined to give 356.7 g/h and analyzed by GC. The yield of glycidol based on 3-chloropropanediol converted was calculated.

The Basic Parameters and Results are Illustrated in the Following Table:

| | |
|---|---|
| Temperature in the dehydrochlorinating reactor | 20-21° C. |
| Temperature in the dehydrating reactor | 48-53° C. |
| Pressure in the dehydrating reactor | 6.7-7.2 kPa |
| Molar ratio of sodium hydroxide vs. 3-chloropropanediol | 0.805 |
| Yield of glycidol (mol/mol of 3-chloropropanediol converted) | 96.84% |

Undefined loss 15.5 g/h (2.75%)

Example 12

In the experimental unit according to Example 1, 215.5 g/h of 3-chloropropanediol with purity of 96.56% and 123.0 g/h of sodium hydroxide aqueous solution with concentration of 49.52% were reacted. The molar ratio between sodium hydroxide and 3-chloropropanediol was 0.809. The reaction mixture was then transferred into the second reactor. The reaction water in amount of 35.0 ml/h was removed by azeotropic vacuum distillation with 155.8 g/h of cyclohexane and the mixture of reaction products with water content lower than 23% was collected. By deep cooling of exhaust gas 42.7 g/h of cyclohexane and water was trapped. 419.5 g/h of the collected product was then filtered and the filter cake was washed by means of 37.1 g/h of cyclohexane to give 101.2 g/h of wet sodium chloride to be further dried, while the filtrate and the washing fluid were combined to give 338.6 g/h Settling into two layers, 122.1 g of the upper cyclohexane layer with small glycidol and salt content, and 216.5 g of the lower product layer with majority of the glycidol were obtained and analyzed by GC. The yield of glycidol based on 3-chloropropanediol converted was calculated.
The Basic Parameters and Results are Illustrated in the Following Table:

| | |
|---|---|
| Temperature in the dehydrochlorinating reactor | 20-22° C. |
| Temperature in the dehydrating reactor | 24-32° C. |
| Pressure in the dehydrating reactor | 12.9-14.3 kPa |
| Molar ratio of sodium hydroxide vs. 3-chloropropanediol | 0.809 |
| Yield of glycidol (mol/mol of 3-chloropropanediol converted) | 81.08% |

Undefined loss 13.9 g/h (2.62%)

Example 13

In the experimental unit according to Example 1, 218.0 g/h of 3-chloropropanediol with purity of 96.56% and 126.0 g/h of sodium hydroxide aqueous solution with concentration of 49.52% were reacted. The molar ratio between sodium hydroxide and 3-chloropropanediol was 0.818. The reaction mixture with alkalinity 0.23 mg NaOH/g was transferred into the second reactor. The reaction water in amount of 72.5 ml/h was removed by azeotropic vacuum distillation with 160.4 g/h of methyl isobutyl ketone (MIBK) and the mixture of reaction products with water content lower than 4% was collected. By deep cooling of exhaust gas 12.2 g/h of ketone and water was trapped. 408.7 g/h of the collected product was then filtered and the filter cake was washed by means of 40.1 g/h of the ketone to give 91.7 g/h of wet sodium chloride to be further dried, while the filtrate and the washing fluid were combined to give 350.1 g/h and analyzed by GC. The yield of glycidol based on 3-chloropropanediol converted was calculated.
The Basic Parameters and Results are Illustrated in the Following Table:

| | |
|---|---|
| Temperature in the dehydrochlorinating reactor | 20-21° C. |
| Temperature in the dehydrating reactor | 33-38° C. |
| Pressure in the dehydrating reactor | 4.4-4.5 kPa |
| Molar ratio of sodium hydroxide vs. 3-chloropropanediol | 0.818 |
| Yield of glycidol (mol/mol of 3-chloropropanediol converted) | 93.93% |

Undefined loss 18.0 g/h (3.31%)
The Comparison of Different Azeotropic Agent Use is Given in the Following Table:

| | Example 11 | Example 12 | Example 13 |
|---|---|---|---|
| Molar ratio of NaOH vs. 3-chloropropanediol | 0.805 | 0.809 | 0.818 |
| Yield of glycidol % (mol/mol of MCH converted) | 96.84 | 81.08 | 93.93 |
| Glycidol content in reaction water in % | 0.18 | 3.16 | 0.17 |
| TOC in dry salt in mg/kg | 251 | 7560 | 192 |

It is obvious the best result was obtained using Example 11 iso-butanol as an azeotropic agent for dehydration. Less satisfactory but still acceptable result was obtained using Example 13 methyl isobutyl ketone. Quite poor result was obtained using Example 12 cyclohexane due to insufficient dehydration efficiency, low reaction yield of the glycidol and extremely low quality of produced salt, probably caused by its limited miscibility with reaction mixture resulting in formation of two liquid phases in dehydration reactor.

Epichlorohydrin—Glycidol Hybrid 2-Stage Dehydrochlorinating Reaction Under Different Molar Ratio MCH:DCH in Feedstock Example 14

233.3 g/h of mixture of 3-chloropropanediol with content of 53.45% and 1,3-dichloropropanol with content of 45.6% (molar ratio MCH:DCH=1.2:0.8=1.5) and 119.0 g/h of sodium hydroxide aqueous solution with concentration of 50.02% were fed continuously into a first reactor of the production cascade. The five-neck glass reactor was equipped with a glass stirrer, thermometer, 3-chloropropanediol+1,3-dichloropropanol mixture inlet, sodium hydroxide solution inlet, product outlet and was situated in a bath filled with cold water. The molar ratio between sodium hydroxide and sum of 3-chloropropanediol+1,3-dichloropropanol was 0.796.

The reaction mixture with residual alkalinity was transferred under control mode by vacuum into a second dehydrating reactor. The five-neck glass reactor was equipped with a glass stirrer, thermometer, reaction mixture inlet, azeotropic agent inlet, and product overflow and was situated in a heating bath filled with hot water. The reactor was fitted with distilling equipment for azeotropic removal of reaction water. The reaction water in amount of 86.7 ml/h was removed by azeotropic vacuum distillation by means of produced epichlorohydrin. No other azeotropic agent was added. The mixture of reaction products with water content lower than 1% was collected in round-bottom flask situated in a cooling bath filled with water-ice mixture. Further portion of azeotropic agent was trapped by deep cooling of exhaust gas from the distilling equipment was 23.8 g/h of epichlorohydrin and 3.5 g/h of water.

236.4 g/h of the collected product was then filtered and the filter cake was washed by means of 34.0 g/h of iso-propanol to give 88.1 g/h of wet sodium chloride to be further dried, while the filtrate and the washing fluid were combined to give 179.5 g/h and analyzed by GC. The molar yields of glycidol based on 3-chloropropanediol converted and epichlorohydrin based on 1,3-dichloropropanol converted were calculated. Epichlorohydrin trapped by deep cooling of the exhaust gas was taken into consideration too.

Filtrate is then processed in the similar way like in Example 10.
The Basic Parameters and Results are Illustrated in the Following Table:

| | |
|---|---|
| Temperature in the dehydrochlorinating reactor | 19-21° C. |
| Temperature in the dehydrating reactor | 42-52° C. |
| Pressure in the dehydrating reactor | 3.7-4.0 kPa |
| Molar ratio of sodium hydroxide vs. MCH + DCH | 0.796 |
| Molar ratio MCH:DCH in feedstock | 1.5 |
| Yield of glycidol + epichlorohydrin (mol/mol of 3-chloropropanediol + 1,3-dichloropropanol converted) | 96.97% |
| Molar ratio glycidol:epichlorohydrin produced | 1.42 |

Undefined loss 4.7 g/h (1.22%)

Example 15

224.5 g/h of mixture of 3-chloropropanediol with content of 45.82% and 1,3-dichloropropanol with content of 53.02% (molar ratio MCH:DCH=1.0:1.0=1.0) and 119.5 g/h of sodium hydroxide aqueous solution with concentration of 49.77% were fed continuously into a first reactor of the production cascade. The five-neck glass reactor was equipped with a glass stirrer, thermometer, 3-chloropropanediol+1,3-dichloropropanol mixture inlet, sodium hydroxide solution inlet, product outlet and was situated in a bath filled with cold water. The molar ratio between sodium hydroxide and sum of 3-chloropropanediol+1,3-dichloropropanol was 0.802.

The reaction mixture with residual alkalinity was transferred under control mode by vacuum into a second dehydrating reactor. The five-neck glass reactor was equipped with a glass stirrer, thermometer, reaction mixture inlet, azeotropic agent inlet, and product overflow and was situated in a heating bath filled with hot water. The reactor was fitted with distilling equipment for azeotropic removal of reaction water. The reaction water in amount of 82.5 ml/h was removed by azeotropic vacuum distillation by means of produced epichlorohydrin. No other azeotropic agent was added. The mixture of reaction products with water content lower than 1% was collected in round-bottom flask situated in a cooling bath filled with water-ice mixture. Further portion of azotropic agent was trapped by deep cooling of exhaust gas from the distilling equipment was 27.9 g/h of epichlorohydrin and 4.4 g/h of water.

237.5 g/h of the collected product was then filtered and the filter cake was washed by means of 35.3 g/h of isopropanol to give 90.6 g/h of wet sodium chloride to be further dried, while the filtrate and the washing fluid were combined to give 179.1 g/h and analyzed by GC. The molar yields of glycidol based on 3-chloropropanediol converted and epichlorohydrin based on 1,3-dichloropropanol converted were calculated. Epichlorohydrin trapped by deep cooling of the exhaust gas was taken into consideration too.

Filtrate is then processed in the similar way like in Example 10.
The Basic Parameters and Results are Illustrated in the Following Table:

| | |
|---|---|
| Temperature in the dehydrochlorinating reactor | 19-20° C. |
| Temperature in the dehydrating reactor | 45-52° C. |
| Pressure in the dehydrating reactor | 4.1-4.4 kPa |
| Molar ratio of sodium hydroxide vs. MCH + DCH | 0.802 |
| Molar ratio MCH:DCH in feedstock | 1.008 |
| Yield of glycidol + epichlorohydrin (mol/mol of 3-chloropropanediol + 1,3-dichloropropanol converted) | 97.42% |
| Molar ratio glycidol:epichlorohydrin produced | 1.13 |

Undefined loss 5.2 g/h (1.37%)

Example 16

226.5 g/h of mixture of 3-chloropropanediol with content of 35.69% and 1,3-dichloropropanol with content of 63.402% (molar ratio MCH:DCH=0.8:1.2=0.667) and 116.0 g/h of sodium hydroxide aqueous solution with concentration of 49.77% were fed continuously into a first reactor of the production cascade. The five-neck glass reactor was equipped with a glass stirrer, thermometer, 3-chloropropanediol+1,3-dichloropropanol mixture inlet, sodium hydroxide solution inlet, product outlet and was situated in a bath filled with cold water. The molar ratio between sodium hydroxide and sum of 3-chloropropanediol+1,3-dichloropropanol was 0.782.

The reaction mixture with residual alkalinity was transferred under control mode by vacuum into a second dehydrating reactor. The five-neck glass reactor was equipped with a glass stirrer, thermometer, reaction mixture inlet, azeotropic agent inlet, and product overflow and was situated in a heating bath filled with hot water. The reactor was fitted with distilling equipment for azeotropic removal of reaction water. The reaction water in amount of 75.0 ml/h was removed by azeotropic vacuum distillation by means of produced epichlorohydrin. No other azeotropic agent was added. The mixture of reaction products with water content lower than 1% was collected in round-bottom flask situated in a cooling bath filled with water-ice mixture. Further portion of azeotropic agent was trapped by deep cooling of exhaust gas from the distilling equipment was 30.7 g/h of epichlorohydrin and 4.8 g/h of water.

223.0 g/h of the collected product was then filtered and the filter cake was washed by means of 35.3 g/h of isopropanol to give 83.1 g/h of wet sodium chloride to be further dried, while the filtrate and the washing fluid were combined to give 172.7 g/h and analyzed by GC. The molar yields of glycidol based on 3-chloropropanediol converted and epichlorohydrin based on 1,3-dichloropropanol converted were calculated. Epichlorohydrin trapped by deep cooling of the exhaust gas was taken into consideration too.

During the dehydration process a formation of sticky salt slurry was observed especially in the second dehydrating reactor. It was more difficult to keep the process running under steady state, especially dehydrated mixture withdrawal line to filtration was several times fouled.

Filtrate is then processed in the similar way like in Example 10.
The Basic Parameters and Results are Illustrated in the Following Table:

| | |
|---|---|
| Temperature in the dehydrochlorinating reactor | 20-21° C. |
| Temperature in the dehydrating reactor | 44-51° C. |
| Pressure in the dehydrating reactor | 4.0-4.1 kPa |
| Molar ratio of sodium hydroxide vs. MCH + DCH | 0.782 |
| Molar ratio MCH:DCH in feedstock | 0.667 |
| Yield of glycidol + epichlorohydrin (mol/mol of 3-chloropropanediol + 1,3-dichloropropanol converted) | 97.34% |
| Molar ratio glycidol:epichlorohydrin produced | 0.89 |

Undefined loss 11.5 g/h (3.04%)

Comparison Table:

| | Example 14 | Example 15 | Example 16 |
|---|---|---|---|
| Molar ration MCH:DCH in feedstock | 1.2:0.8 | 1.0:1.0 | 0.8:1.2 |
| Yield of glycidol + epichlorohydrin (mol/mol of 3-chloropropanediol + 1,3-dichloropropanol converted) | 96.97% | 97.42% | 97.34% |
| Molar ratio glycidol:epichlorohydrin theoretical | 1.50 | 1.00 | 0.66 |
| Molar ratio glycidol:epichlorohydrin produced | 1.42 | 1.13 | 0.89 |

Glycidylesters Formation Under Different Azeotropic Agents

Example 17

In the experimental unit according to Example 1, 216.0 g/h of a mixture consisting of 66.3% of 3-chloro-1,2-propanediol and 29.2% of 2-chloro-1,3-propanediol with content of chlorohydrin esters 2.5% and 119.55 g/h of sodium hydroxide aqueous solution with concentration of 49.77% were reacted. The molar ratio between sodium hydroxide and sum of 3-chloro-1,2-propanediol and 2-chloro-1,3-propanediol was 0.798. The reaction mixture with residual alkalinity was transferred into the second reactor. The reaction water in amount of 85.0 ml/h was removed by azeotropic vacuum distillation with 160.4 g/h of methyl isobutyl ketone and the mixture of reaction products with water content lower than 2.0% was collected. By deep cooling of exhaust gas 31.9 g/h of methyl isobutyl ketone and 4.3 g/h of water was trapped. 384.2 g/h of the collected product was then filtered and the filter cake was washed with 36.1 g/h of methyl isobutyl ketone to give 88.1 g/h of wet sodium chloride to be further dried, while the filtrate and the washing fluid were combined to give 327.2 g/h and analyzed by GC. The yield of glycidol based on sum of monochloropropanediols converted was calculated.

The Basic Parameters and Results are Illustrated in the Following Table:

| | |
|---|---|
| Temperature in the dehydrochlorinating reactor | 20-21° C. |
| Temperature in the dehydrating reactor | 34-42° C. |
| Pressure in the dehydrating reactor | 4.8-5.3 kPa |
| Molar ratio of sodium hydroxide vs. chloropropanediols | 0.798 |
| Yield of glycidol (mol/mol of chloropropanediols converted) | 89.60% |
| Glycidylester content in filtrate | 0.22% |

Undefined loss 4.5 g/h (0.85%)

Example 18

In the experimental unit according to Example 1, 216.7 g/h of a mixture consisting of 66.3% of 3-chloro-1,2-propanediol and 29.2% of 2-chloro-1,3-propanediol with content of chlorohydrin esters 2.5% and 120.7 g/h of sodium hydroxide aqueous solution with concentration of 49.77% were reacted. The molar ratio between sodium hydroxide and sum of 3-chloro-1,2-propanediol and 2-chloro-1,3-propanediol was 0.803. The reaction mixture with residual alkalinity was transferred into the second reactor. The reaction water in amount of 115.0 ml/h was removed by azeotropic vacuum distillation with 160.4 g/h of iso-butanol and the mixture of reaction products with water content lower than 3.0% was collected. By deep cooling of exhaust gas 5.6 g/h of iso-butanol and 0.2 g/h of water was trapped. 399.0 g/h of the collected product was then filtered and the filter cake was washed with 40.1 g/h of iso-butanol to give 103.3 g/h of wet sodium chloride to be further dried, while the filtrate and the washing fluid were combined to give 334.6 g/h and analyzed by GC. The yield of glycidol based on sum of monochloropropanediols converted was calculated.

The Basic Parameters and Results are Illustrated in the Following Table:

| | |
|---|---|
| Temperature in the dehydrochlorinating reactor | 19-20° C. |
| Temperature in the dehydrating reactor | 38-44° C. |
| Pressure in the dehydrating reactor | 4.8-4.9 kPa |
| Molar ratio of sodium hydroxide vs. chloropropanediols | 0.803 |
| Yield of glycidol (mol/mol of chloropropanediols converted) | 90.69% |
| Glycidylester content in filtrate | 0.11% |

Undefined loss 20.8 g/h (3.87%)

Example 19

In the experimental unit according to Example 1, 216.0 g/h of a mixture consisting of 66.3% of 3-chloro-1,2-propanediol and 29.2% of 2-chloro-1,3-propanediol with content of chlorohydrin esters 2.5% and 120.0 g/h of sodium hydroxide aqueous solution with concentration of 49.77% were reacted. The molar ratio between sodium hydroxide and sum of 3-chloro-1,2-propanediol and 2-chloro-1,3-propanediol was 0.801. The reaction mixture with residual alkalinity was transferred into the second reactor. The reaction water in amount of 92.5 ml/h was removed by azeotropic vacuum distillation with 162.0 g/h of n-butanol (n-BuOH) and the mixture of reaction products with water content lower than 2.0% was collected. By deep cooling of exhaust gas 2.8 g/h of n-butanol and 0.1 g/h of water was trapped. 412.9 g/h of the collected product was then filtered and the filter cake was washed with 40.5 g/h of iso-butanol to give 96.7 g/h of wet sodium chloride to be further dried, while the filtrate and the washing fluid were combined to give 355.6 g/h and analyzed by GC. The yield of glycidol based on sum of monochloropropanediols converted was calculated.

The Basic Parameters and Results are Illustrated in the Following Table:

| | |
|---|---|
| Temperature in the dehydrochlorinating reactor | 19-20° C. |
| Temperature in the dehydrating reactor | 44-48° C. |
| Pressure in the dehydrating reactor | 4.7-4.9 kPa |
| Molar ratio of sodium hydroxide vs. chloropropanediols | 0.801 |
| Yield of glycidol (mol/mol of –chloropropanediols converted) | 91.45% |
| Glycidylester content in filtrate | 0.05% |

Undefined loss 9.2 g/h (1.71%)

The Comparison of Different Azeotropic Agent Use is Given in the Following Table:

| | Example 17 | Example 18 | Example 19 |
|---|---|---|---|
| Type of the agent | MIBK | iso-BuOH | n-BuOH |
| Molar ratio of NaOH vs. chloropropanediols | 0.798 | 0.803 | 0.801 |
| Yield of glycidol % (mol/mol of MCH converted) | 89.60 | 90.69 | 91.45 |
| Glycidylester content % in filtrate | 0.22 | 0.11 | 0.05 |

It is obvious the best result in term of glycidylester formation was obtained using n-butanol as an azeotropic agent for dehydration step. Less satisfactory but still acceptable result was obtained using iso-butanol. Quite poor result was obtained using methyl isobutyl ketone due to different chemical structure/chemistry.

Glycidol Yield Under Different 2MCH:3MCH Ratio in Feedstock

Example 20

In the experimental unit according to Example 1, 224.0 g/h of a mixture consisting of 96.6% of 3-chloro-1,2-propanediol and 0.05% of 2-chloro-1,3-propanediol and 125.5 g/h of sodium hydroxide aqueous solution with concentration of 49.60% were reacted. The molar ratio between sodium hydroxide and 3-chloropropanediol was 0.795. The reaction mixture with residual alkalinity was transferred into the second reactor. The reaction water in amount of 85.0 ml/h was removed by azeotropic vacuum distillation with 144.9 g/h of iso-butanol and the mixture of reaction products with water content lower than 3.0% was collected. By deep cooling of exhaust gas 10.8 g/h of iso-butanol and water was trapped. 380.2 g/h of the collected product was then filtered and the filter cake was washed by means of 40.3 g/h of iso-butanol to give 86.5 g/h of wet sodium chloride to be further dried, while the filtrate and the washing fluid were combined to give 328.7 g/h and analyzed by GC. The molar yield of glycidol based on 3-chloropropanediol converted was calculated.
The Basic Parameters and Results are Illustrated in the Following Table:

| | |
|---|---|
| Temperature in the dehydrochlorinating reactor | 20-21° C. |
| Temperature in the dehydrating reactor | 33-36° C. |
| Pressure in the dehydrating reactor | 2.7 kPa |
| Molar ratio of sodium hydroxide vs. 3-chloropropanediol | 0.795 |
| 2MCH:3MCH ration in feedstock | 0.0005 |
| Yield of glycidol (mol/mol of 3-chloropropanediol converted) | 97.66% |

Undefined loss 23.7 g/h (4.43%)

Example 21

In the experimental unit according to Example 1, 201.0 g/h of a mixture consisting of 82.4% of 3-chloro-1,2-propanediol and 9.2% of 2-chloro-1,3-propanediol and 111.5 g/h of sodium hydroxide aqueous solution with concentration of 49.45% were reacted. The molar ratio between sodium hydroxide and sum of 3-chloro-1,2-propanediol and 2-chloro-1,3-propanediol was 0.827. The reaction mixture with residual alkalinity was transferred into the second reactor. The reaction water in amount of 72.5 ml/h was removed by azeotropic vacuum distillation with 161.0 g/h of iso-butanol and the mixture of reaction products with water content lower than 3.0% was collected. By deep cooling of exhaust gas 8.2 g/h of iso-butanol and 5.3 g/h of water was trapped. 387.8 g/h of the collected product was then filtered and the filter cake was washed with 40.3 g/h of iso-butanol to give 89.3 g/h of wet sodium chloride to be further dried, while the filtrate and the washing fluid were combined to give 335.5 g/h and analyzed by GC. The yield of glycidol based on sum of monochloropropanediols converted was calculated.
The basic parameters and results are illustrated in the following Table:

| | |
|---|---|
| Temperature in the dehydrochlorinating reactor | 19-21° C. |
| Temperature in the dehydrating reactor | 43-49° C. |
| Pressure in the dehydrating reactor | 6.5-6.7 kPa |
| Molar ratio of sodium hydroxide vs. chloropropanediols | 0.827 |
| 2MCH:3MCH ration in feedstock | 0.11 |
| Yield of glycidol (mol/mol of chloropropanediols converted) | 94.27% |

Undefined loss 3.0 g/h (0.58%)

Example 22

In the experimental unit according to Example 1, 216.7 g/h of a mixture consisting of 65.3% of 3-chloro-1,2-propanediol and 28.7% of 2-chloro-1,3-propanediol and 120.7 g/h of sodium hydroxide aqueous solution with concentration of 49.77% were reacted. The molar ratio between sodium hydroxide and sum of 3-chloro-1,2-propanediol and 2-chloro-1,3-propanediol was 0.814. The reaction mixture with residual alkalinity was transferred into the second reactor. The reaction water in amount of 115.0 ml/h was removed by azeotropic vacuum distillation with 160.4 g/h of iso-butanol and the mixture of reaction products with water content lower than 3.0% was collected. By deep cooling of exhaust gas 5.6 g/h of iso-butanol and 0.2 g/h of water was trapped. 399.0 g/h of the collected product was then filtered and the filter cake was washed with 40.5 g/h of iso-butanol to give 103.3 g/h of wet sodium chloride to be further dried, while the filtrate and the washing fluid were combined to give 334.6 g/h and analyzed by GC. The yield of glycidol based on sum of monochloropropanediols converted was calculated.
The Basic Parameters and Results are Illustrated in the Following Table:

| | |
|---|---|
| Temperature in the dehydrochlorinating reactor | 19-20° C. |
| Temperature in the dehydrating reactor | 38-44° C. |
| Pressure in the dehydrating reactor | 4.8-4.9 kPa |
| Molar ratio of sodium hydroxide vs. chloropropanediols | 0.814 |
| 2MCH:3MCH ration in feedstock | 0.44 |
| Yield of glycidol (mol/mol of chloropropanediols converted) | 90.69% |

Undefined loss 20.8 g/h (3.87%)

Example 23

In the experimental unit according to Example 1, 222.5 g/h of a mixture consisting of 49.7% of 3-chloro-1,2-propanediol and 45.2% of 2-chloro-1,3-propanediol and 124.0 g/h of sodium hydroxide aqueous solution with concentration of 49.45% were reacted. The molar ratio between sodium hydroxide and sum of 3-chloro-1,2-propanediol and 2-chloro-1,3-propanediol was 0.802. The reaction mixture with residual alkalinity was transferred into the second reactor. The reaction water in amount of 85.0 ml/h was removed by azeotropic vacuum distillation with 148.9 g/h of iso-butanol and the mixture of reaction products with water content lower than 4.0% was collected. By deep cooling of exhaust gas 3.2 g/h of iso-butanol and 0.2 g/h of water was trapped. 415.0 g/h of the collected product was then filtered and the filter cake was washed with 40.3 g/h of iso-butanol to give 95.2 g/h of wet sodium chloride to be further dried, while the filtrate and the washing fluid were combined to give 358.4 g/h and analyzed by GC. The yield of glycidol based on sum of monochloropropanediols converted was calculated.
The Basic Parameters and Results are Illustrated in the Following Table:

| | |
|---|---|
| Temperature in the dehydrochlorinating reactor | 19-21° C. |
| Temperature in the dehydrating reactor | 42-49° C. |
| Pressure in the dehydrating reactor | 6.4-6.7 kPa |
| Molar ratio of sodium hydroxide vs. chloropropanediols | 0.802 |
| 2MCH:3MCH ration in feedstock | 0.91 |
| Yield of glycidol (mol/mol of chloropropanediols converted) | 89.87% |

Undefined loss 20.8 g/h (3.87%)
The Comparison of Different 2MCH:3MCH Ratio is Given in the Following Table:

| | Example 20 | Example 21 | Example 22 | Example 23 |
|---|---|---|---|---|
| Type of the agent | iso-BuOH | iso-BuOH | iso-BuOH | iso-BuOH |
| Molar ratio of NaOH vs. chloropropanediols | 0.795 | 0.827 | 0.814 | 0.802 |
| Yield of glycidol % (mol/mol of MCH converted) | 97.66 | 94.27 | 90.69 | 89.87 |
| 2MCH:3MCH ratio in feedstock | 0.0005 | 0.11 | 0.44 | 0.91 |

It is obvious the best result in term of glycidol yield was obtained using almost pure 3-chloro-1,2-propanediol (3MCH), and the glycidol yield monotonously decreases with higher amount of 2-chloro-1,3-propanediol in the feedstock.

Batchwise Dehydrochiorinating Reaction and Water Removal (Dehydration) in One Step Example 24

The five-neck glass 1 liter reactor was equipped with a glass stirrer, thermometer, 3-chloropropanediol inlet, sodium hydroxide solution inlet, product outlet and has water jacket connected to thermostat. The reactor was fitted with distilling column for azeotropic removal of reaction water under the reduced pressure. No deep cooling to trap the non-condensed vapours was installed.

200.0 g of 3-chloropropanediol with purity of 99.0% and 160.0 g of n-butanol were inserted to the reactor. Then the system was stirred, evacuated, heated to start the boiling and next the n-butanol was distilled—i.e. started to reflux. Then 191.8 g of sodium hydroxide aqueous solution with concentration of 37.28% was fed semi-continuously into the reactor within 86 minutes. The reaction water in amount of 115 ml was removed by azeotropic vacuum distillation. The molar ratio between sodium hydroxide and 3-chloropropanediol was 0.998.

As soon as NaOH feed was completed the system was kept on parameters another 5 minutes and then 347.1 g of the reaction mixture with residual alkalinity less than 1 mg NaOH/g was withdrawn, neutralized and filtered. Filter cake was washed by means of 59.4 g of n-butanol to give 125.6 g of wet sodium chloride to be further dried, while the filtrate and the washing fluid were combined to give 309.4 g of filtered dehydrated mixture and analyzed by GC. The molar yield of glycidol based on 3-chloropropanediol converted was calculated.

The Basic Parameters and Results are Illustrated in the Following Table:

| | |
|---|---|
| Temperature in the dehydrochlorinating + dehydrating reactor | 28-38° C. |
| Pressure in the dehydrating reactor | 1.7-1.9 kPa |
| Molar ratio of sodium hydroxide vs. 3-chloropropanediol | 0.998 |
| Yield of glycidol (mol/mol of 3-chloropropanediol converted) | 92.65% |

Undefined loss 61.2 g (10.01%)

Example 25

In the experimental unit according to Example 24, 265.9 g of 3-chloropropanediol with purity of 99.0% and 329.7 g of iso-butanol were inserted to the reactor. Then the system was stirred, evacuated, heated to start the boiling and next the iso-butanol was distilled—i.e. started to reflux. Then 385.4 g of sodium hydroxide aqueous solution with concentration of 24.51% was fed semi-continuously into the reactor within 84 minutes. The reaction water in amount of 316 g was removed by azeotropic vacuum distillation. The molar ratio between sodium hydroxide and 3-chloropropanediol was 0.991.

As soon as NaOH feed was completed the system was kept on parameters another 5 minutes and then 590.2 g of the reaction mixture with residual alkalinity less than 0.5 mg NaOH/g was withdrawn, neutralized and filtered. Filter cake was washed by means of 58.2 g of iso-butanol to give 160.4 g of wet sodium chloride to be further dried, while the filtrate and the washing fluid were combined to give 487.0 g of filtered dehydrated mixture and analyzed by GC. The molar yield of glycidol based on 3-chloropropanediol converted was calculated.

The Basic Parameters and Results are Illustrated in the Following Table:

| | |
|---|---|
| Temperature in the dehydrochlorinating + dehydrating reactor | 27-35° C. |
| Pressure in the dehydrating reactor | 2.1-2.3 kPa |
| Molar ratio of sodium hydroxide vs. 3-chloropropanediol | 0.991 |
| Yield of glycidol (mol/mol of 3-chloropropanediol converted) | 90.73% |

Undefined loss 75.8 g (7.29%)

Example 26

In the experimental unit according to Example 24, 230.0 g of 3-chloropropanediol with purity of 98.04% and 335.8 g of iso-butanol were inserted to the reactor. Then the system was stirred, evacuated, heated to start the boiling and next the iso-butanol was distilled—i.e. started to reflux. Then 328.3 g of sodium hydroxide aqueous solution with concentration of 24.74% was fed semi-continuously into the reactor within 90 minutes. The reaction water in amount of 254.7 g was removed by azeotropic vacuum distillation. By deep cooling of exhaust gas 57.3 g of iso-butanol and 28.1 g of water was trapped. The molar ratio between sodium hydroxide and 3-chloropropanediol was 0.995.

As soon as NaOH feed was completed the system was kept on parameters another 5 minutes and then 521.0 g of the reaction mixture with residual alkalinity less than 0.5 mg NaOH/g was withdrawn, neutralized and filtered. Filter cake was washed by means of 60.6 g of iso-butanol to give 131.2 g of wet sodium chloride to be further dried, while the filtrate and the washing fluid were combined to give 428.2 g of filtered dehydrated mixture and analyzed by GC. The molar yield of glycidol based on 3-chloropropanediol converted was calculated.

The Basic Parameters and Results are Illustrated in the Following Table:

| | |
|---|---|
| Temperature in the dehydrochlorinating + dehydrating reactor | 18-32° C. |
| Pressure in the dehydrating reactor | 1.0-1.6 kPa |
| Molar ratio of sodium hydroxide vs. 3-chloropropanediol | 0.995 |
| Yield of glycidol (mol/mol of 3-chloropropanediol converted) | 93.87% |

Undefined loss 55.2 g (5.78%)

Example 27

In the experimental unit according to Example 24, 170.0 g of 3-chloropropanediol with purity of 99.0% and 380.5 g of iso-butanol were inserted to the reactor. Then the system was stirred, evacuated, heated to start the boiling and next the isobutanol was distilled—i.e. started to reflux. Then 225.8 g of sodium hydroxide aqueous solution with concentration of 24.80% was fed semi-continuously into the reactor within 75 minutes. The reaction water in amount of 159.4 g was removed by azeotropic vacuum distillation. The molar ratio between sodium hydroxide and 3-chloropropanediol was 0.919.

As soon as NaOH feed was completed the system was kept on parameters another 5 minutes and then 493.3 g of the reaction mixture with residual alkalinity less than 0.1 mg NaOH/g was withdrawn, neutralized and filtered. Filter cake was washed by means of 59.2 g of iso-butanol to give 88.7 g of wet sodium chloride to be further dried, while the filtrate and the washing fluid were combined to give 473.2 g of filtered dehydrated mixture and analyzed by GC. The molar yield of glycidol based on 3-chloropropanediol converted was calculated.

The Basic Parameters and Results are Illustrated in the Following Table:

| | |
|---|---|
| Temperature in the dehydrochiorinating + dehydrating reactor | 20-30° C. |
| Pressure in the dehydrating reactor | 1.6-2.0 kPa |
| Molar ratio of sodium hydroxide vs. 3-chloropropanediol | 0.919 |
| Yield of glycidol (mol/mol of 3-chloropropanediol converted) | 96.32% |

Undefined loss 114.2 g (13.67%)

Example 28

In the experimental unit according to Example 24, a series of lab trials with different amount of azeotropic agent added was performed. 230.0 g of 3-chloropropanediol with purity of 98.04% and calculated amount of iso-butanol were inserted to the reactor. Then the system was stirred, evacuated, heated to start the boiling and next the iso-butanol was distilled—i.e. started to reflux. Then 338.0 g of sodium hydroxide aqueous solution with concentration of 24.26% was fed semi-continuously into the reactor within 90 minutes. The reaction water was removed by azeotropic vacuum distillation. The molar ratio between sodium hydroxide and 3-chloropropanediol was 0.995.

As soon as NaOH feed was completed the system was kept on parameters another 5 minutes and then the reaction mixture with residual alkalinity less than 0.1 mg NaOH/g was withdrawn, neutralized and filtered. Filter cake was washed by means of 59.2 g of iso-butanol to give wet sodium chloride, while the filtrate and the washing fluid were combined to give filtered dehydrated mixture and analyzed by GC. The molar yield of glycidol based on 3-chloropropanediol converted was calculated.

The Basic Parameters and Results are Illustrated in the Following Table:

| | | | | | | |
|---|---|---|---|---|---|---|
| Temperature in the dehydrochlorinating + dehydrating reactor | | | 20-33° C. | | | |
| Pressure in the dehydrating reactor | | | 1.1-1.6 kPa | | | |
| Molar ratio of sodium hydroxide vs. 3-chloropropanediol | | | 0.995 | | | |
| Trial | 1 | 2 | 3 | 4 | 5 | 6 |
| Targeted content of glycidol % in filtrate before cake washing | 30 | 35 | 40 | 45 | 50 | 55 |
| Yield of glycidol % (mol/mol of MCH converted) | 92.12 | 89.39 | 87.06 | 85.85 | 83.47 | 80.92 |

It is obvious there is a strong influence of glycidol yield on the amount of azeotropic agent added, which represents a glycidol concentration in the filtrate—higher the concentration of glycidol in the filtrate, lower the yield of glycidol due to serial reactions of glycidol.

2-Stage Dehydrochlorinating Reaction in First Plug Flow Reactor

Example 29

205.0 g/h of 3-chloropropanediol with purity of 97.57% and 117.0 g/h of sodium hydroxide aqueous solution with concentration of 49.45% were fed continuously into a first reactor of the production cascade. The reactor consists of vertical jacketed tube, equipped by the jacketed mixer of the reactants on the top of the tube, thermometer, 3-chloropropanediol inlet to such mixer, sodium hydroxide solution inlet to such mixer, reaction mixture outlet at the tube bottom. The jacket and the mixer were tempered/cooled independently by means of two thermostat circulations. The 3MCH liquid feed was cooled down to 0° C. just before mixer inlet, NaOH solution was cooled down to 13° C. just before mixer inlet. The molar ratio between sodium hydroxide and 3-chloropropanediol was 0.799. The mean residence time was 1 hour.

The reaction mixture with residual alkalinity was transferred under control mode by vacuum into a second reactor/dehydration step. The five-neck glass reactor was equipped with a glass stirrer, thermometer, reaction mixture inlet, azeotropic agent inlet, and product overflow and was situated in a heating bath filled with hot water. The reactor was fitted with distilling equipment for azeotropic removal of reaction water. The reaction water in amount of 85.0 ml/h was removed by azeotropic vacuum distillation with 161.0 g/h of iso-butanol, which was fed into the second reactor continuously. The mixture of reaction products with water content lower than 2.0% was collected in round-bottom flask situated in a cooling bath filled with water-ice mixture. Further portion of azeotropic agent trapped by deep cooling of exhaust gas from the distilling equipment was 3.0 g/h of iso-butanol and 1.3 g/h of water.

386.1 g/h of the collected product was then filtered and the filter cake was washed by means of 40.3 g/h of iso-butanol to give 94.7 g/h of wet sodium chloride to be further dried, while the filtrate and the washing fluid were combined to give 330.2 g/h and analyzed by GC. The molar yield of glycidol based on 3-chloropropanediol converted was calculated.

The Basic Parameters and Results are Illustrated in the Following Table:

| | |
|---|---|
| Temperature in the dehydrochlorinating reactor | 19-22° C. |
| Temperature in the dehydrating reactor | 45-47° C. |
| Pressure in the dehydrating reactor | 6.8-6.9 kPa |
| Molar ratio of sodium hydroxide vs. 3-chloropropanediol | 0.799 |
| Yield of glycidol (mol/mol of 3-chloropropanediol converted) | 96.74% |
| TOC in dry salt | 304 mg/kg |

Undefined loss 9.1 g/h (1.74%)

The invention claimed is:

1. A process for manufacturing epoxy monomers and/or epoxides, wherein the process comprises the following steps:
   a. reacting chlorohydrin with an alkaline agent to form an epoxide and precipitated chloride salt;
   b. dehydrating the reaction mixture of step (a) in the presence of a binary azeotropic mixture comprising water and an azeotropic agent, added to the reaction mixture or generated in situ in step (a), resulting in the production of a dehydrated reaction mixture;

c. filtering the dehydrated reaction mixture from step b) to produce a chloride salt and a filtered liquid fraction; and d. isolating the epoxide from the filtered liquid fraction.

2. The process of claim 1, wherein the filtered liquid fraction of step (c) is subjected to evaporation under reduced pressure with a short residence time of the boiling liquid phase, the resulting vapours are either fed directly to step (d) or condensed to collect a liquid fraction and subsequently the liquid fraction is fed do step (d).

3. The process of claim 1, wherein said dehydration in step (b) is carried out by distillation under reduced pressure.

4. The process of claim 1, wherein said isolation of the epoxide in step (d) is carried out by distillation under reduced pressure.

5. The process of claim 3, wherein the at least one distillate stream or fraction is recycled back to step (a).

6. The process of claim 3, wherein at least one distillate stream/fraction is recycled back to step (b).

7. The process of claim 1, wherein the molar equivalents ratio of the sum of chlorohydrines and acids towards said alkaline agent is between 1.001 and 1.30.

8. The process of claim 1, wherein the reaction in step (a) is carried out at −10 to 100° C.

9. The process of claim 1, wherein the dehydration in step (b) is carried out at 0-100° C.

10. The process of claim 1, wherein, for batch-wise process, steps (a) and (b) are carried out in one combined reaction-dehydration zone.

11. The process of claim 1, wherein, for continuous process, steps (a) and (b) are carried out in separate zones.

12. The process of claim 11, wherein the mean residence time in step (a) is from 0.1 to 5 hours.

13. The process of claim 1, wherein said alkaline agent is selected from alkali metal or alkali earth metal hydroxides and carbonates.

14. The process of claim 13, wherein said alkaline agent is sodium hydroxide.

15. The process of claim 1, wherein the amount of azeotropic agent in the dehydrated mixture from step (b) to be further filtered is in the range of 20-80%.

16. The process of claim 1 for manufacturing glycidol, wherein said chlorohydrin is monochloropropanediol or mixture of monochloropropanediol and dichloropropanol.

17. The process of claim 16, wherein the content of alkali metals and alkali-earth metals in any chemical or physical form in the glycidol mixture to be distilled in step (d) is less than 0.1%.

18. The process of claim 16, wherein the azeotropic agent has limited solubility with water, normal boiling point less than 150° C., and is fully miscible with glycidol under the process conditions.

19. The process of claim 16, wherein said azeotropic agent is selected from alcohols, ketones, epoxides, aliphatic hydrocarbons and aromatic and cyclic hydrocarbons.

20. The process of claim 16, wherein monochloropropanediol feedstock has a content of impurities less than 10%, wherein the sum of glycerine-or chlorohydrin-esters is less than 6%.

21. The process of claim 16, wherein monochloropropanediol feedstock has a ratio of 2-chloro-1,3-propanediol towards 3-chlor-1,2-propanediol lower than 1.0.

22. The process of claim 16, wherein said monochloropropanediol has been obtained as a reactive intermediate of synthesis of dichloropropanol by hydrochlorination of glycerine in the presence of a carboxylic acid catalyst.

23. The process of claim 19, wherein the azeotropic agent is selected from n-butanol, iso-butanol, sec-butanol, methylisobutylketone, n-heptane, dichloroethane, cyclohexane and epichlorohydrin.

24. The process of claim 23, wherein the azeotropic agent is n-butanol or iso-butanol or a mixture thereof.

25. The process of claim 1, wherein chlorohydrines feedstock has molar ratio of monochloropranediol towards dichloropropanol higher than 0.6.

26. The process of claim 1, wherein the said chlorohydrins are chlorohydrinethers and epoxides are glycidylethers.

27. The process of claim 1, wherein the said epoxides are epoxyalcohols.

28. The process of claim 27, wherein said epoxyalcohol is glycidol.

* * * * *